US011840511B2

(12) United States Patent
Yamashita et al.

(10) Patent No.: US 11,840,511 B2
(45) Date of Patent: *Dec. 12, 2023

(54) HALOACETALDEHYDE ALKYL 2-CYCLOPENTENYL ACETAL COMPOUND AND A PROCESS FOR PREPARING THE SAME, A PROCESS FOR PREPARING A (2-CYCLOPENTENYL)ACETATE ESTER COMPOUND THEREFROM, AND A PROCESS FOR PREPARING A (2-CYCLOPENTENYL)ACETIC ACID COMPOUND THEREFROM

(71) Applicant: Shin-Etsu Chemical Co., Ltd., Tokyo (JP)

(72) Inventors: Miyoshi Yamashita, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/805,513

(22) Filed: Jun. 6, 2022

(65) Prior Publication Data

US 2023/0002304 A1  Jan. 5, 2023

(30) Foreign Application Priority Data

Jun. 9, 2021 (JP) ................. 2021-096712

(51) Int. Cl.
*C07C 67/14* (2006.01)
*C07C 51/09* (2006.01)
*C07C 67/00* (2006.01)
*C07C 41/52* (2006.01)
*C07C 43/313* (2006.01)

(52) U.S. Cl.
CPC .............. *C07C 67/14* (2013.01); *C07C 41/52* (2013.01); *C07C 43/313* (2013.01); *C07C 51/09* (2013.01); *C07C 67/00* (2013.01); *C07C 2601/10* (2017.05)

(58) Field of Classification Search
None
See application file for complete search history.

(56) References Cited

PUBLICATIONS

Stork ("Regiospecific trapping of Radicals from Cyclization Reactions. Cyclic Nitriles via Isocyanide Trapping" J. Am. Chem. Soc. 1983, 105, p. 6765-6766) (Year: 1983).*
STN Registry No. 87453-51-8 (entered STN Nov. 16, 1984) (Year: 1984).*
Rynchnovsky ("Free-Radical Cyclization of Bromoacetals. Use in the Construction of Bicyclic Acetals and Lactones" J. Am. Chem. Soc. 1983, 105, p. 3742-3743) (Year: 1983).*
Mook ("Vinyl Radical Cyclization. 2. Dicyclization via Selective Formation of Unsaturated Vinyl Radicals by Intramolecular Addition to Triple Bonds. Applications to the Synthesis of Butenolides and Furans" J. Am. Chem. Soc. 1983, 105, p. 3720-3722) (Year: 1983).*
Rowlands ("The Use of Alkyl Vinyl Ethers in Olefin Syntheses" J. Org. Chem 1952, 17, p. 807-811) (Year: 1952).*
Curran ("Regiocontrol in Opening of 2H-cyclopenta[b]furanones with Organocopper Reagents" J. Org. Chem. 1986(51), p. 1614-1615) (Year: 1986).*
Ainai ("Efficient Total Synthesis of 12-oxo-PDA and OPC-8:0" J. Org. Chem. 2003(68), p. 7825-7832) (Year: 2003).*
Kobayashi ("Synthesis of Δ2-OPC-8:0 and OPC-6:0" Synlett, 2004 (14), p. 2582-2584) (Year: 2004).*
STN Registry No. 1071154-56-7, publicly available as of Nov. 6, 2008 (Year: 2008).*
Johnson et al. "A Simple Stereoselective Version of the Claisen Rearrangement Leading to trans-Trisubstituted Olefinic Bonds. Synthesis of Squalene" Journal of the American Chemical Society, 92(3):741-743 (1970).
Mori et al. "Pheromone synthesis. Part 262: Determination of the absolute configuration of the female sex pheromone" Tetrahedron, 73:6530-6541 (2017).
Mori, Kenji "Pheromone synthesis. Part 260: Synthesis of (±)-(anti-1,2-dimethyl-3-methylenecyclopentyl) acetaldehyde" Tetrahedron, 72:6578-6588 (2016).
Ramesh et al. "Syntheses and Determination of Absolute Configurations and Biological Activities of the Enantiomers of the Longtailed Mealybug Pheromone" Journal of Organic Chemistry, 78(12):6281-6284 (2013).
Tabata et al. "Sex pheromone of a coccoid insect with sexual and asexual lineages: fate of an ancestrally essential sexual signal in parthenogenetic females" Journal of the Royal Society Interface, 14:20170027 (2017).
Zou et al. "Improved Synthesis of the Pheromone of the Longtailed Mealybug" Synlett, 15:2319-2321 (2010).
Ramesh et al. "Enantiospecific Synthesis of Both Enantiomers of the Longtailed Mealybug Pheromone and Their in a New Zealand Vineyard" the Journal of Organic Chemistry, 80:7785-7789 (2015) Evaluation.
Extended European Search Report corresponding to European Patent Application No. 22177595.0 (5 pages) (dated Nov. 30, 2022).

* cited by examiner

*Primary Examiner* — Amy C Bonaparte
(74) *Attorney, Agent, or Firm* — Myers Bigel, P.A.

(57) ABSTRACT

The present invention relates to a process for preparing a (2-cyclopentenyl)acetate ester compound of general formula (2) as described herein, the process comprising: subjecting a haloacetaldehyde alkyl 2-cyclopentenyl acetal compound of general formula (1) as described herein to a dehydrohalogenation reaction in the presence of a base, followed by a rearrangement reaction to form the (2-cyclopentenyl)acetate ester compound of general formula (2). The present invention also relates to a process for preparing a (2-cyclopentenyl)acetic acid compound of general formula (3) as described herein, the process comprising hydrolyzing the (2-cyclopentenyl)acetate ester compound of general formula (2) to form the (2-cyclopentenyl)acetic acid compound of general formula (3). The present invention also relates to a haloacetaldehyde alkyl 2-cyclopentenyl acetal compound of general formula (1) as described herein.

16 Claims, No Drawings

HALOACETALDEHYDE ALKYL 2-CYCLOPENTENYL ACETAL COMPOUND AND A PROCESS FOR PREPARING THE SAME, A PROCESS FOR PREPARING A (2-CYCLOPENTENYL)ACETATE ESTER COMPOUND THEREFROM, AND A PROCESS FOR PREPARING A (2-CYCLOPENTENYL)ACETIC ACID COMPOUND THEREFROM

TECHNICAL FIELD

The present invention relates to a haloacetaldehyde alkyl 2-cyclopentenyl acetal compound which is a novel compound, and a process for preparing the same. The present invention relates also to a process for preparing a (2-cyclopentenyl)acetate ester compound therefrom, and a process for preparing a (2-cyclopentenyl)acetic acid compound therefrom.

BACKGROUND ART

Mealybugs are pests belonging to the order Hemiptera, the family Pseudococcidae, and suck juice of many agricultural plants, such as grapes, apples, pears, persimmons, pineapples, bananas, coffee, citrus, and flowering plants, to damage these agricultural plants. Further, mealybugs discharge honeydew which contains sugar to cause fungi-induced diseases. These damage and diseases reduce the yield and quality of such agricultural plants, which is a serious problem.

Generally, insecticides have been used for controlling mealybugs. However, mealybugs live in narrow spaces behind leaves and/or plant barks and are themselves covered with a waxy substance. Therefore, insecticides are difficult to come in contact with the pest body. This results in insufficient effects of the insecticides.

In the light of adverse effects of insecticides on the environment and human health, there is recently a demand for the development of a new highly safe, and eco-friendly control method such as mating disruption and/or mass trapping using sex pheromones of insects. Development of such a new control method requires the industrial and inexpensive preparation of a sex pheromone in a large amount.

For sex pheromones of mealybugs, the chemical structures of sex pheromones secreted from about 20 species of agriculturally harmful mealybugs have been identified. Some of these sex pheromones are known to have a characteristic structure wherein a cyclopentane or cyclopentene ring is substituted with an alkyl group and a 2-acyloxyethyl group or a formylmethyl group attaches to the ring.

Specifically, a sex pheromone of the longtailed mealybug (scientific name: *Pseudococcus longispinus*) is reported to be an optically active (−)-2-(1,5,5-trimethyl-2-cyclopentenyl)ethyl acetate (Non-Patent Literature 1 listed below). A sex pheromone of a sexually reproducing strain of the pineapple mealybug (scientific name: *Dysmicoccus brevipes*) is reported to be an optically active (1S,2S)-(−)-(1,2-dimethyl-3-methylenecyclopentyl)acetaldehyde (Non-Patent Literatures 2 and 3 listed below).

Enantiomers or diastereomers (i.e., kinds of stereoisomers) of such optically active sex pheromone are reported to have no adverse effect on the attracting activity of natural pheromones (Non-Patent Literatures 1 and 3). Accordingly, for establishment of the techniques for controlling the pests utilizing sex pheromones it is thought to be efficient to find a process for preparing a mixture of stereoisomers containing the natural pheromones in view of the inexpensive supply of the pheromone substances and for a economical control method.

A process for preparing a mixture of stereoisomers of these pheromones is reported as follows. For example, a mixture of stereoisomers containing (−)-2-(1,5,5-trimethyl-2-cyclopentenyl)ethyl acetate, which is a sex pheromone substance of the longtailed mealybug, is prepared by acetylating 3,4,4-trimethyl-2-cyclopenten-1-ol, reacting the reaction product with a base and, then, t-butyldimethylsilyl chloride, subjecting the reaction product to an Ireland-Claisen rearrangement reaction to form (1,5,5-trimethyl-2-cyclopentenyl)acetic acid as an intermediate, and then converting a functional group of the intermediate into a target functional group (Non-Patent Literature 4 listed below).

A mixture of stereoisomers containing (1S,2S)-(−)-(1,2-dimethyl-3-methylenecyclopentyl)acetaldehyde, which is a sex pheromone of the pineapple mealybug, is prepared by acetylating 2,3-dimethyl-2-cyclopeten-1-ol, reacting the reaction product with a base and, then, trimethylsilyl chloride, subjecting the reaction product to an Ireland-Claisen rearrangement reaction to form (1,2-dimethyl-2-cyclopentenyl)acetic acid as an intermediate, transforming the skeleton of the intermediate into the skeleton of a target compound and, then, converting a functional group in the resulting compound into a target functional group to obtain a mixture of enantiomers and/or diastereomers (Non-Patent Literature 5 listed below).

Like the aforesaid Ireland-Claisen rearrangement reaction, a Johnson-Claisen rearrangement reaction is known as a Claisen-type rearrangement reaction of allylalcohols such as 2-cyclopenten-1-ol compounds, in which a 2-cyclopenten-1-ol compound is reacted with a trialkyl orthoacetate in the presence of a weakly acidic catalyst such as propionic acid to form a (2-cyclopentenyl)acetate ester compound (Non-Patent Literature 6 listed below).

LIST OF THE LITERATURES

Non-Patent Literatures

[Non-Patent Literature 1] R. Ramesh et al., J. Org. Chem., 2013, 78, 6281-6284.
[Non-Patent Literature 2] J. Tabata et al., J. R. Soc. Interface, 14 (2017), a copy of which is downloadable from the following URLhttps://royalsocietypublishing.org/doi/10.1098/rsif.2017.0027.
[Non-Patent Literature 3] K. Mori et al., Tetrahedron, 73 (2017) 6530-6541.
[Non-Patent Literature 4] J. G. Millar et al., Synlett, 15 (2010) 2319-2321.
[Non-Patent Literature 5] K. Mori et al., Tetrahedron, 72 (2016) 6578-6588.
[Non-Patent Literature 6] W. S. Johnson et al., J. Am. Chem. Soc., 92 (1970) 741-743.

Problems to be Solved by the Invention

As mentioned above, in all of the literatures, the (2-cyclopentenyl)acetic acid compound is used as a useful synthetic intermediate to prepare the envisaged sex pheromones of mealybugs. There is need for establishing a process for industrially and inexpensively preparing a (2-cyclopentenyl) acetate ester compound and a (2-cyclopentenyl)acetic acid compound.

However, the preparation processes described in Non-Patent Literature 4 and Non-Patent Literature 5 using an Ireland-Claisen rearrangement reaction have such disadvantages that an organolithium compound and lithium amide, which are ignitable, are used; the reactions must be carried out at a so extremely low temperature as −78° C.; and industrially relatively expensive trialkylsilane chloride is used.

In the process described in Non-Patent Literature 6 for preparing a (2-cyclopentenyl)acetate ester by a Johnson-Claisen rearrangement reaction in which a 2-cyclopenten-1-ol compound is reacted with a trialkyl orthoacetate in the presence of a weakly acidic catalyst, a dehydration reaction of the starting material, 2-cyclopeten-1-ol compound, occurs preferentially to cause a problematic low yield (see, Non-Patent Literature 4 and the Comparative Examples 1 and 2 described in the present specification).

Thus, the prior art failed to industrially and economically prepare a (2-cyclopentenyl)acetate ester compound and a (2-cyclopentenyl)acetic acid compound in a large amount.

SUMMARY OF THE INVENTION

The present invention has been made in these circumstances, and aims to overcome the aforesaid problems of the prior art and to provide a novel starting material compound for preparing a (2-cyclopentenyl)acetate ester compound and a (2-cyclopentenyl)acetic acid compound, which compounds are intermediates for preparing the pheromones of mealybugs.

The present invention also aims to overcome the aforesaid problems of the prior art and to provide a process for industrially and economically preparing a (2-cyclopentenyl) acetate ester compound and a process for industrially and economically preparing a (2-cyclopentenyl)acetic acid compound, which are intermediates for preparing the pheromones of mealybugs.

As a result of the intensive researches, the present inventors have now provide a haloacetaldehyde alkyl 2-cyclopentenyl acetal compound which is a novel compound, and have found that it is possible to prepare a (2-cyclopentenyl) acetate ester compound, without using an ignitable starting material and an industrially expensive starting material, in an industrially readily applicable range of a reaction temperature, by subjecting the haloacetaldehyde alkyl 2-cyclopentenyl acetal compound to a dehydrohalogenation reaction in the presence of a base, followed by a rearrangement reaction.

The present inventors have also found that it is possible to efficiently and industrially prepare a (2-cyclopentenyl)acetic acid compound by hydrolyzing the (2-cyclopentenyl)acetate ester compound thus prepared, and thus have completed the present invention.

According to one aspect of the present invention, the present invention provides a process for preparing a (2-cyclopentenyl)acetate ester compound of the following general formula (2):

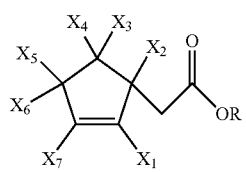

wherein R represents a linear or branched alkyl group having 1 to 4 carbon atoms, and $X_1$ to $X_7$ represent, independently of each other, a hydrogen atom or a methyl group, with the proviso that one to three among $X_1$ to $X_7$ represent a methyl group and the remaining represent a hydrogen atom, the process comprising:

subjecting a haloacetaldehyde alkyl 2-cyclopentenyl acetal compound of the following general formula (1):

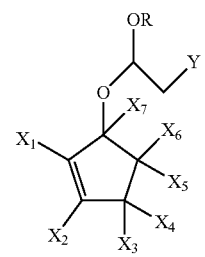

wherein R is as defined above, $X_1$ to $X_7$ are as selected in the general formula (2), respectively, and Y represents a halogen atom, to a dehydrohalogenation reaction in the presence of a base, followed by a rearrangement reaction to form the (2-cyclopentenyl)acetate ester compound (2).

According to another aspect of the present invention, the present invention provides a process for preparing a (2-cyclopentenyl)acetic acid compound of the following general formula (3):

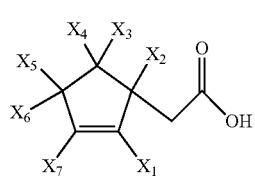

wherein $X_1$ to $X_7$ are as selected in the general formula (1), respectively, the process comprising:

the aforesaid process for preparing the (2-cyclopentenyl)acetate ester compound (2); and hydrolyzing the (2-cyclopentenyl)acetate ester compound (2) to form the (2-cyclopentenyl)acetic acid compound (3).

According to another aspect of the present invention, the present invention provides a process for preparing a haloacetaldehyde alkyl 2-cyclopentenyl acetal compound of the following general formula (1):

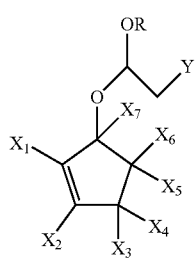

(1)

wherein R represents a linear or branched alkyl group having 1 to 4 carbon atoms, $X_1$ to $X_7$ represent, independently of each other, a hydrogen atom or a methyl group, with the proviso that one to three among $X_1$ to $X_7$ represent a methyl group and the remaining represent a hydrogen atom, and Y represents a halogen atom, the process comprising:

halogenating an alkyl vinyl ether compound of the following general formula (4):

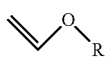

(4)

wherein is as defined above, with a halogenating agent to form a halide; and
subjecting the halide to a substitution reaction with a 2-cyclopenten-1-ol compound of the following general formula (5):

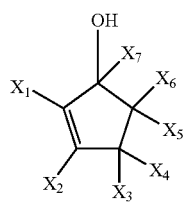

(5)

wherein $X_1$ to $X_7$ are as selected in the general formula (1), respectively, to form the haloacetaldehyde alkyl 2-cyclopentenyl acetal compound (1).

According to another aspect of the present invention, the present invention provides a process for preparing a (2-cyclopentenyl)acetate ester compound of the following general formula (2):

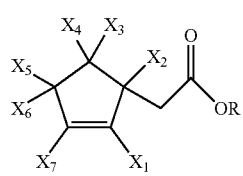

(2)

wherein R represents a linear or branched alkyl group having 1 to 4 carbon atoms, $X_1$ to $X_7$ are as selected in the general formula (1), respectively, the process comprising:

the aforesaid process for preparing the haloacetaldehyde alkyl 2-cyclopentenyl acetal compound (1); and subjecting the haloacetaldehyde alkyl 2-cyclopentenyl acetal compound (1) to a dehydrohalogenation reaction in the presence of a base, followed by a rearrangement reaction to form the (2-cyclopentenyl) acetate ester compound (2).

According to another aspect of the present invention, the present invention provides a process for preparing a (2-cyclopentenyl)acetic acid compound of the following general formula (3):

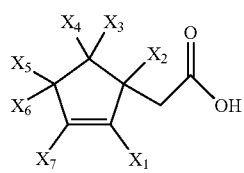

(3)

wherein $X_1$ to $X_7$ are as selected in the general formula (1), respectively, the process comprising:

the aforesaid process for preparing the (2-cyclopentenyl)acetate ester compound (2); and hydrolyzing the (2-cyclopentenyl)acetate ester compound (2) to form the (2-cyclopentenyl)acetic acid compound (3).

According to another aspect of the present invention, the present invention provides a haloacetaldehyde alkyl 2-cyclopentenyl acetal compound (1) of the following general formula (1):

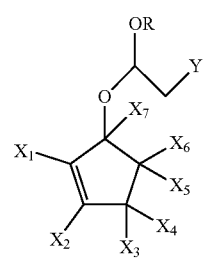

(1)

wherein R represents a linear or branched alkyl group having 1 to 4 carbon atoms, $X_1$ to $X_7$ represent, independently of each other, a hydrogen atom or a methyl group, with the proviso that one to three among $X_1$ to $X_7$ represent a methyl group and the remaining represent a hydrogen atom, and Y represents a halogen atom.

According to the present invention, haloacetaldehyde alkyl 2-cyclopentenyl acetal compound (1) which is a novel compound is provided.

According to the present invention, it is possible to prepare (2-cyclopentenyl)acetate ester compound (2), which is an effective a useful intermediate for preparing the pheromones of mealybugs, using the haloacetaldehyde alkyl 2-cyclopentenyl acetal compound (1) as a starting material without an ignitable starting material and an industrially expensive starting material, in an industrially readily applicable range of a reaction temperature.

According to the present invention, it is also possible to industrially and economically prepare the (2-cyclopentenyl)

acetic acid compound (3) by hydrolyzing the (2-cyclopentenyl)acetate ester compound (2) thus prepared.

Haloacetaldehyde alkyl 2-cyclopentenyl acetal compound (1) which is a novel compound is useful also as an intermediate for preparing a prostaglandin analogue.

DETAILED DESCRIPTION OF THE PREFERRED EMBODIMENTS

Embodiments of the present invention will be described in detail below. It should be noted that the present invention is not limited to or by the embodiments.

A. Haloacetaldehyde alkyl 2-cyclopentenyl acetal compound which is a novel compound and of the following general formula (1) will be described below.

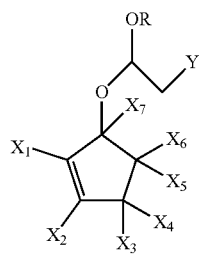

(1)

In the general formula (1), R represents a linear or branched alkyl group having 1 to 4 carbon atoms. Examples of the alkyl group include linear alkyl groups such as a methyl group, an ethyl group, an n-propyl group, and an n-butyl group; and branched alkyl groups such as an isopropyl group and an isobutyl group. A methyl group, an ethyl group, and an n-propyl group are preferred in view of the reactivity and/or the yield.

In the general formula (1), $X_1$ to $X_7$ represent, independently of each other, a hydrogen atom or a methyl group, with the proviso that one to three among $X_1$ to $X_7$ represent a methyl group and the remaining represent a hydrogen atom.

When one of $X_1$ to $X_7$ is a methyl group, any one of $X_1$, $X_2$, $X_3$, $X_4$, $X_5$, $X_6$, and $X_7$ is a methyl group. For example, in Example 1-7 described below, $X_2$ is a methyl group, and the remaining represent a hydrogen atom.

In a case where two of $X_1$ to $X_7$ represent a methyl group, when $X_1$ is a methyl group, any one of $X_2$, $X_3$, $X_4$, $X_5$, $X_6$, and $X_7$ is a methyl group; when $X_2$ is a methyl group, any one of $X_1$, $X_3$, $X_4$, $X_5$, $X_6$, and $X_7$ is a methyl group; when $X_3$ is a methyl group, any one of $X_1$, $X_2$, $X_4$, $X_5$, $X_6$, and $X_7$ is a methyl group; when $X_4$ is a methyl group, any one of $X_1$, $X_2$, $X_3$, $X_5$, $X_6$, and $X_7$ is a methyl group; when $X_5$ is a methyl group, any one of $X_1$, $X_2$, $X_3$, $X_4$, $X_6$, and $X_7$ is a methyl group; when $X_6$ is a methyl group, any one of $X_1$, $X_2$, $X_3$, $X_4$, $X_5$, and $X_7$ is a methyl group; and when $X_7$ is a methyl group, any one of $X_1$, $X_2$, $X_3$, $X_4$, $X_5$, and $X_6$ is a methyl group. For example, in Example 1-5 described below, $X_1$ and $X_2$ represent a methyl group, and the remaining represent a hydrogen atom; and in Example 1-6 described below, $X_5$ and $X_6$ represent a methyl group, and the remaining represent a hydrogen atom.

In a case where three of $X_1$ to $X_7$ represent a methyl group, when $X_1$ and $X_2$ represent a methyl group, any one of $X_3$, $X_4$, $X_5$, $X_6$, and $X_7$ is a methyl group; when $X_1$ and $X_3$ represent a methyl group, any one of $X_2$, $X_4$, $X_5$, $X_6$, and $X_7$ is a methyl group; when $X_1$ and $X_4$ represent a methyl group, any one of $X_2$, $X_3$, $X_5$, $X_6$, and $X_7$ is a methyl group; when $X_1$ and $X_5$ represents a methyl group, any one of $X_2$, $X_3$, $X_4$, $X_6$, and $X_7$ is a methyl group; when $X_1$ and $X_6$ represents a methyl group, any one of $X_2$, $X_3$, $X_4$, $X_5$, and $X_7$ is a methyl group; when $X_1$ and $X_7$ represent a methyl group, any one of $X_2$, $X_3$, $X_4$, $X_5$, and $X_6$ is a methyl group; and all other combinations besides the combination of three methyl groups described above are also possible. For example, in Examples 1-1, 1-2, 1-3, and 1-4, $X_2$, $X_3$, and $X_4$ represent a methyl group, and the remaining represent a hydrogen atom.

In another embodiment, $X_7$ among $X_1$ to $X_7$ is preferably a hydrogen atom.

In another embodiment, particularly, $X_1$ and $X_7$ among $X_1$ to $X_7$ preferably represent a hydrogen atom. More preferably, $X_1$, $X_5$, $X_6$, and $X_7$ represent a hydrogen atom, and $X_2$, $X_3$, and $X_4$ represent a methyl group (see, Example 1-1, Example 1-2, Example 1-3, and Example 1-4 below).

In another embodiment, particularly, $X_4$ and $X_7$ among $X_1$ to $X_7$ preferably represent a hydrogen atom. Preferably, $X_3$, $X_4$, $X_5$, $X_6$, and $X_7$ represent a hydrogen atom, and $X_1$ and $X_2$ represent a methyl group (see, Example 1-5 below). Preferably, $X_1$, $X_2$, $X_3$, $X_4$, and $X_7$ represent a hydrogen atom, and $X_5$ and $X_6$ represent a methyl group (see, Example 1-6 below). Alternatively, $X_1$, $X_3$, $X_4$, $X_5$, $X_6$, and $X_7$ preferably represent a hydrogen atom, and $X_2$ represents a methyl group (see, Example 1-7 below).

In the general formula (1), Y represents a halogen atom. Examples of the halogen atom include a chlorine atom, a bromine atom, and an iodine atom. A bromine atom or an iodine atom is preferred in view of the reactivity and/or the yield.

Examples of the haloacetaldehyde alkyl 2-cyclopentenyl acetal compound (1) include the following compounds:

chloroacetaldehyde linear alkyl monomethyl-2-cyclopentenyl acetal compounds such as chloroacetaldehyde methyl 3-methyl-2-cyclopentenyl acetal, chloroacetaldehyde ethyl 3-methyl-2-cyclopentenyl acetal, chloroacetaldehyde 3-methyl-2-cyclopentenyl n-propyl acetal, chloroacetaldehyde n-butyl 3-methyl-2-cyclopentenyl acetal, chloroacetaldehyde methyl 5-methyl-2-cyclopentenyl acetal, chloroacetaldehyde ethyl 5-methyl-2-cyclopentenyl acetal, chloroacetaldehyde 5-methyl-2-cyclopentenyl n-propyl acetal, and chloroacetaldehyde n-butyl 5-methyl-2-cyclopentenyl acetal;

bromoacetaldehyde linear alkyl monomethyl-2-cyclopentenyl acetal compounds such as bromoacetaldehyde methyl 3-methyl-2-cyclopentenyl acetal, bromoacetaldehyde ethyl 3-methyl-2-cyclopentenyl acetal, bromoacetaldehyde 3-methyl-2-cyclopentenyl n-propyl acetal, bromoacetaldehyde n-butyl 3-methyl-2-cyclopentenyl acetal, bromoacetaldehyde methyl 5-methyl-2-cyclopentenyl acetal, bromoacetaldehyde ethyl 5-methyl-2-cyclopentenyl acetal, bromoacetaldehyde 5-methyl-2-cyclopentenyl n-propyl acetal, and bromoacetaldehyde n-butyl 5-methyl-2-cyclopentenyl acetal;

iodoacetaldehyde linear alkyl monomethyl-2-cyclopentenyl acetal compounds such as iodoacetaldehyde methyl 3-methyl-2-cyclopentenyl acetal, iodoacetaldehyde ethyl 3-methyl-2-cyclopentenyl acetal, iodoacetaldehyde 3-methyl-2-cyclopentenyl n-propyl acetal, iodoacetaldehyde n-butyl 3-methyl-2-cyclopentenyl acetal, iodoacetaldehyde methyl 5-methyl-2-cyclopentenyl acetal, iodoacetaldehyde ethyl 5-methyl-2-cyclopentenyl acetal, iodoacetaldehyde 5-methyl-2-cyclopentenyl n-propyl acetal, and iodoacetaldehyde n-butyl 5-methyl-2-cyclopentenyl acetal;

chloroacetaldehyde branched alkyl monomethyl-2-cyclopentenyl acetal compounds such as chloroacetaldehyde isopropyl 3-methyl-2-cyclopentenyl acetal, chloroacetaldehyde isobutyl 3-methyl-2-cyclopentenyl acetal, chloroacetaldehyde isopropyl 5-methyl-2-cyclopentenyl acetal, and chloroacetaldehyde isobutyl 5-methyl-2-cyclopentenyl acetal;

bromoacetaldehyde branched alkyl monomethyl-2-cyclopentenyl acetal compounds such as bromoacetaldehyde isopropyl 3-methyl-2-cyclopentenyl acetal, bromoacetaldehyde isobutyl 3-methyl-2-cyclopentenyl acetal, bromoacetaldehyde isopropyl 5-methyl-2-cyclopentenyl acetal, and bromoacetaldehyde isobutyl 5-methyl-2-cyclopentenyl acetal;

iodoacetaldehyde branched alkyl monomethyl-2-cyclopentenyl acetal compounds such as iodoacetaldehyde isopropyl 3-methyl-2-cyclopentenyl acetal, iodoacetaldehyde isobutyl 3-methyl-2-cyclopentenyl acetal, iodoacetaldehyde isopropyl 5-methyl-2-cyclopentenyl acetal, and iodoacetaldehyde isobutyl 5-methyl-2-cyclopentenyl acetal;

chloroacetaldehyde linear alkyl dimethyl-2-cyclopentenyl acetal compounds such as chloroacetaldehyde 2,3-dimethyl-2-cyclopentenyl methyl acetal, chloroacetaldehyde 2,3-dimethyl-2-cyclopentenyl ethyl acetal, chloroacetaldehyde 2,3-dimethyl-2-cyclopentenyl n-propyl acetal, chloroacetaldehyde n-butyl 2,3-dimethyl-2-cyclopentenyl acetal, chloroacetaldehyde 5,5-dimethyl-2-cyclopentenyl methyl acetal, chloroacetaldehyde 5,5-dimethyl-2-cyclopentenyl ethyl acetal, chloroacetaldehyde 5,5-dimethyl-2-cyclopentenyl n-propyl acetal, and chloroacetaldehyde n-butyl 5,5-dimethyl-2-cyclopentenyl acetal;

bromoacetaldehyde linear alkyl dimethyl-2-cyclopentenyl acetal compounds such as bromoacetaldehyde 2,3-dimethyl-2-cyclopentenyl methyl acetal, bromoacetaldehyde 2,3-dimethyl-2-cyclopentenyl ethyl acetal, bromoacetaldehyde 2,3-dimethyl-2-cyclopentenyl n-propyl acetal, bromoacetaldehyde n-butyl 2,3-dimethyl-2-cyclopentenyl acetal, bromoacetaldehyde 5,5-dimethyl-2-cyclopentenyl methyl acetal, bromoacetaldehyde 5,5-dimethyl-2-cyclopentenyl ethyl acetal, bromoacetaldehyde 5,5-dimethyl-2-cyclopentenyl n-propyl acetal, and bromoacetaldehyde n-butyl 5,5-dimethyl-2-cyclopentenyl acetal;

iodoacetaldehyde linear alkyl dimethyl-2-cyclopentenyl acetal compounds such as iodoacetaldehyde 2,3-dimethyl-2-cyclopentenyl methyl acetal, iodoacetaldehyde 2,3-dimethyl-2-cyclopentenyl ethyl acetal, iodoacetaldehyde 2,3-dimethyl-2-cyclopentenyl n-propyl acetal, iodoacetaldehyde n-butyl 2,3-dimethyl-2-cyclopentenyl acetal, iodoacetaldehyde 5,5-dimethyl-2-cyclopentenyl methyl acetal, iodoacetaldehyde 5,5-dimethyl-2-cyclopentenyl ethyl acetal, iodoacetaldehyde 5,5-dimethyl-2-cyclopentenyl n-propyl acetal, and iodoacetaldehyde n-butyl 5,5-dimethyl-2-cyclopentenyl acetal; chloroacetaldehyde branched alkyl dimethyl-2-cyclopentenyl acetal compounds such as chloroacetaldehyde 2,3-dimethyl-2-cyclopentenyl isopropyl acetal, chloroacetaldehyde 2,3-dimethyl-2-cyclopentenyl isobutyl acetal, chloroacetaldehyde 5,5-dimethyl-2-cyclopentenyl isopropyl acetal, and chloroacetaldehyde 5,5-dimethyl-2-cyclopentenyl isobutyl acetal;

bromoacetaldehyde branched alkyl dimethyl-2-cyclopentenyl acetal compounds such as bromoacetaldehyde 2,3-dimethyl-2-cyclopentenyl isopropyl acetal, bromoacetaldehyde 2,3-dimethyl-2-cyclopentenyl isobutyl acetal, bromoacetaldehyde 5,5-dimethyl-2-cyclopentenyl isopropyl acetal, and bromoacetaldehyde 5,5-dimethyl-2-cyclopentenyl isobutyl acetal;

iodoacetaldehyde branched alkyl dimethyl-2-cyclopentenyl acetal compounds such as iodoacetaldehyde 2,3-dimethyl-2-cyclopentenyl isopropyl acetal, iodoacetaldehyde 2,3-dimethyl-2-cyclopentenyl isobutyl acetal, iodoacetaldehyde 5,5-dimethyl-2-cyclopentenyl isopropyl acetal, and iodoacetaldehyde 5,5-dimethyl-2-cyclopentenyl isobutyl acetal;

chloroacetaldehyde linear alkyl trimethyl-2-cyclopentenyl acetal compounds such as chloroacetaldehyde methyl 3,4,4-trimethyl-2-cyclopentenyl acetal, chloroacetaldehyde ethyl 3,4,4-trimethyl-2-cyclopentenyl acetal, chloroacetaldehyde n-propyl 3,4,4-trimethyl-2-cyclopentenyl acetal, chloroacetaldehyde n-butyl 3,4,4-trimethyl-2-cyclopentenyl acetal, chloroacetaldehyde methyl 2,3,4-trimethyl-2-cyclopentenyl acetal, chloroacetaldehyde ethyl 2,3,4-trimethyl-2-cyclopentenyl acetal, chloroacetaldehyde n-propyl 2,3,4-trimethyl-2-cyclopentenyl acetal, and chloroacetaldehyde n-butyl 2,3,4-trimethyl-2-cyclopentenyl acetal;

bromoacetaldehyde linear alkyl trimethyl-2-cyclopentenyl acetal compounds such as bromoacetaldehyde methyl 3,4,4-trimethyl-2-cyclopentenyl acetal, bromoacetaldehyde ethyl 3,4,4-trimethyl-2-cyclopentenyl acetal, bromoacetaldehyde n-propyl 3,4,4-trimethyl-2-cyclopentenyl acetal, bromoacetaldehyde n-butyl 3,4,4-trimethyl-2-cyclopentenyl acetal, bromoacetaldehyde methyl 2,3,4-trimethyl-2-cyclopentenyl acetal, bromoacetaldehyde ethyl 2,3,4-trimethyl-2-cyclopentenyl acetal, bromoacetaldehyde n-propyl 2,3,4-trimethyl-2-cyclopentenyl acetal, and bromoacetaldehyde n-butyl 2,3,4-trimethyl-2-cyclopentenyl acetal;

iodoacetaldehyde linear alkyl trimethyl-2-cyclopentenyl acetal compounds such as iodoacetaldehyde methyl 3,4,4-trimethyl-2-cyclopentenyl acetal, iodoacetaldehyde ethyl 3,4,4-trimethyl-2-cyclopentenyl acetal, iodoacetaldehyde n-propyl 3,4,4-trimethyl-2-cyclopentenyl acetal, iodoacetaldehyde n-butyl 3,4,4-trimethyl-2-cyclopentenyl acetal, iodoacetaldehyde methyl 2,3,4-trimethyl-2-cyclopentenyl acetal, iodoacetaldehyde ethyl 2,3,4-trimethyl-2-cyclopentenyl acetal, iodoacetaldehyde n-propyl 2,3,4-trimethyl-2-cyclopentenyl acetal, and iodoacetaldehyde n-butyl 2,3,4-trimethyl-2-cyclopentenyl acetal;

chloroacetaldehyde branched alkyl trimethyl-2-cyclopentenyl acetal compounds such as chloroacetaldehyde isopropyl 3,4,4-trimethyl-2-cyclopentenyl acetal, chloroacetaldehyde isobutyl 3,4,4-trimethyl-2-cyclopentenyl acetal, chloroacetaldehyde isopropyl 2,3,4-trimethyl-2-cyclopentenyl acetal, and chloroacetaldehyde isobutyl 2,3,4-trimethyl-2-cyclopentenyl acetal;

bromoacetaldehyde branched alkyl trimethyl-2-cyclopentenyl acetal compounds such as bromoacetaldehyde isopropyl 3,4,4-trimethyl-2-cyclopentenyl acetal, bromoacetaldehyde isobutyl 3,4,4-trimethyl-2-cyclopentenyl acetal, bromoacetaldehyde isopropyl 2,3,4-trimethyl-2-cyclopentenyl acetal, and bromoacetaldehyde isobutyl 2,3,4-trimethyl-2-cyclopentenyl acetal; and iodoacetaldehyde branched alkyl trimethyl-2-cyclopentenyl acetal compounds such as iodoacetaldehyde isopropyl 3,4,4-trimethyl-2-cyclopentenyl acetal, iodoacetaldehyde isobutyl 3,4,4-trimethyl-2-cyclopentenyl acetal, iodoacetaldehyde isopropyl 2,3,4-trimethyl-2- cyclopentenyl acetal, and iodoacetaldehyde isobutyl 2,3,4-trimethyl-2-cyclopentenyl acetal.

Furthermore, the haloacetaldehyde alkyl 2-cyclopentenyl acetal compound (1) may be its enantiomers, diastereomers, and a mixture of such stereoisomers in the same or different amounts.

Next, a process for preparing the haloacetaldehyde alkyl 2-cyclopentenyl acetal compound (1) will be described below.

The haloacetaldehyde alkyl 2-cyclopentenyl acetal compound (1) is prepared, for example, by halogenating an alkyl vinyl ether compound of the following general formula (4) with a halogenating agent to form a halide and, subsequently, subjecting the halide thus obtained to a substitution reaction with a 2-cyclopenten-1-ol compound of the following general formula (5), as shown in the following reaction formula (see, Example 1-1 to Example 1-7 below).

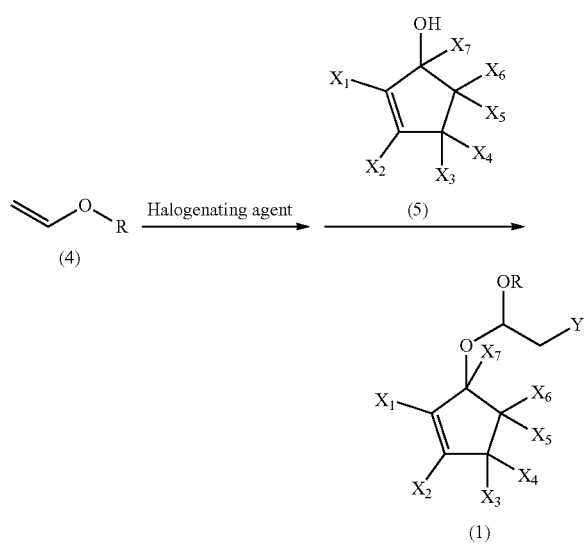

The process for preparing the haloacetaldehyde alkyl 2-cyclopentenyl acetal compound (1) will be further described in detail below.

The alkyl vinyl ether compound (4), which is a starting material, will be described below.

R in the general formula (4) is as defined for the general formula (1).

Examples of the alkyl vinyl ether compound (4) include linear alkyl vinyl ethers such as methyl vinyl ether, ethyl vinyl ether, n-propyl vinyl ether, and n-butyl vinyl ether; and branched alkyl vinyl ethers such as isopropyl vinyl ether and isobutyl vinyl ether.

The alkyl vinyl ether compound (4) may be commercially available one or may be prepared in house.

The halogenation of the alkyl vinyl ether compound (4) may be carried out with a halogenating agent, and may be carried out with heating or cooling, if needed.

Examples of the halogenating agent used in the halogenation include chlorinating agents such as chlorine, sulfuryl chloride, N-chlorosuccinimide, iodobenzene dicholoride, tetrabutylammonium iodotetrachloride, titanium (IV) chloride, and copper (II) chloride; brominating agents such as bromine, N-bromosuccinimide, N-bromoacetamide, 1,3-dibromo-5,5-dimethylhydantoin, tetrabutylammonium tribromide, phenyltrimethylammonium tribromide, iodobenzene dibromide, copper (II) bromide, copper (I) bromide, magnesium (II) bromide, and aluminum bromide; iodinating agents such as iodine, N-iodosuccinimide, and 1,3-diiodo-5,5-dimethylhydantoin; and chloro-iodinating agents such as iodine monochloride and potassium tetrachloroiodate. The brominating agent and the iodinating agent are preferred. Bromine and N-bromosuccinimide among the brominating agent, and iodine and N-iodosuccinimide among the iodinating agents are more preferred in view of the reactivity and/or the yield.

An amount of the halogenating agent used in the halogenation varies, depending on the structure and/or the reactivity of the alkyl vinyl ether compound (4) and/or the halogenating agent, and is preferably from 0.2 mol to 5.0 mol, more preferably from 0.5 mol to 2.0 mol, per mol of the alkyl vinyl ether compound (4) in view of the yield and/or the by-production of an impurity.

A solvent used in the halogenation may be any solvent that has no adverse effect on the halogenation. Examples of the solvent used in the halogenation include halogen-based solvents such as methylene chloride, chloroform, carbon tetrachloride, and 1,2-dichloroethane; ether solvents such as diethyl ether, di-n-butyl ether, di-t-butyl ether, tetrahydrofuran, 1,4-dioxane, and diethyleneglycol dimethyl ether; hydrocarbon solvents such as hexane and heptane; and aprotic polar solvents such as N,N-dimethylformamide, N,N-dimethylacetamide, dimethyl sulfoxide, and hexamethylphosphoric triamide. The halogen-based solvents, the ether solvents, and the aprotic polar solvents are preferred in view of the reactivity.

The solvent may be used either alone or in combination thereof, if necessary, and may be optionally determined while considering the type and/or the reactivity and/or the selectivity of the alkyl vinyl ether compound (4) and/or the halogenating agent.

An amount of the solvent used in the halogenation may be optionally determined while considering the type and/or the reactivity of the alkyl vinyl ether compound (4) and/or the halogenating agent, and is, for example, preferably from 50 g to 10000 g, more preferably from 500 g to 8000 g, per of the alkyl vinyl ether compound (4) in view of the reactivity and/or the by-production of an impurity.

A reaction temperature of the halogenation may be optionally determined while considering the reactivity of the alkyl vinyl ether compound (4) and/or the halogenating agent and/or the formation of an impurity, and is, for example, preferably from −60° C. to 150° C., more preferably from −20° C. to 50° C., in view of the reactivity and/or the formation of an impurity.

The reaction time of the halogenation is preferably optimized, depending on the reactivity of the alkyl vinyl ether compound (4) and/or the halogenating agent, by monitoring the reaction progress with, for example, gas chromatography and/or thin layer chromatography to confirm the disappearance of the alkyl vinyl ether compound (4) and/or the halogenating agent. For example, the reaction time of the halogenation is preferably from 0.5 hours to 168 hours, more preferably from 0.5 hours to 24 hours, even more preferably 0.5 hours to 6 hours, in view of the yield and/or the formation of an impurity.

A halide prepared from the halogenation of the alkyl vinyl ether compound (4) with the halogenating agent is thought to be an alkyl 1,2-dihaloethyl ether of the following general formula (7). The halide may be isolated and/or purified after the halogenation, and then used in a subsequent step or may be used as such in the reaction mixture in a subsequent step without isolation and/or purification after the halogenation.

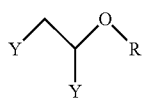

(7)

In the general formula (7), R is as defined for the general formula (4), and Y represents, independently of each other, a halogen atom. Examples of the halogen atom include a chlorine atom, a bromine atom, and an iodine atom. A bromine atom or an iodine atom is preferred in view of the yield and/or the reactivity. Y may be, independently of each other, the same or different. When the halogenating agent is, for example, a chloro-iodinating agent such as iodine monochloride or potassium tetrachloroiodate, Y may be, independently of each other, different.

Next, the 2-cyclopenten-1-ol compound (5) will be described below.

$X_1$ to $X_7$ in the general formula (5) are as defined for the general formula (1). When the haloacetaldehyde alkyl 2-cyclopentenyl acetal compound (1) is prepared from the 2-cyclopenten-1-ol compound (5), each of $X_1$ to $X_7$ in the general formula (1) is a hydrogen atom or a methyl group as defined for the general formula (5).

Examples of the 2-cyclopenten-1-ol compound (5) include monomethyl-2-cyclopenten-1-ol such as 3-methyl-2-cyclopenten-1-ol and 5-methyl-2-cyclopenten-1-ol; dimethyl-2-cyclopenten-1-ol such as 2,3-dimethyl-2-cyclopenten-1-ol and 5,5-dimethyl-2-cyclopenten-1-ol; and trimethyl-2-cyclopenten-1-ol such as 3,4,4-trimethyl-2-cyclopenten-1-ol and 2,3,4-trimethyl-2-cyclopenten-1-ol.

The 2-cyclopenten-1-ol compound (5) may be commercially available one or may be prepared in house.

In the substitution reaction, the halogen atom (i.e., the secondary Y) in the halide is substituted with the 2-cyclopenten-1-ol compound (5) to form the haloacetaldehyde alkyl 2-cyclopentenyl acetal compound (1).

An amount of the 2-cyclopenten-1-ol compound (5) used is preferably from 0.2 mol to 5.0 mol, more preferably from 0.5 mol to 2.0 mol, per mol of the alkyl vinyl ether compound (4) in view of the yield and/or the formation of a by-product and/or the economy.

The substitution reaction may be carried out with heating or cooling, if needed. The substitution reaction may be carried out in the presence of a base while considering the reactivity of the 2-cyclopenten-1-ol compound (5) and the halide and/or the by-production of an impurity.

Examples of the base include amines such as triethylamine, diisopropylethylamine, pyridine, N,N-dimethylaminopyridine, and N,N-dimethylaniline; organometallic compounds such as n-butyl lithium, methyl lithium, and phenyl lithium; metal amides such as lithium diisopropylamide, lithium hexamethyldisilazide, sodium hexamethyldisilazide, and lithium dicyclohexylamide; metal hydroxides such as sodium hydroxide and potassium hydroxide; and metal carbonates such as potassium carbonate, sodium carbonate, and sodium bicarbonate.

The base may be used either alone or in combination thereof, if necessary, and may be optionally determined while considering the reactivity of the 2-cyclopenten-1-ol compound (5) and/or the halide and/or the formation of an impurity.

An amount of the base used may be optionally determined while considering the reactivity of the 2-cyclopenten-1-ol compound (5) and/or the halide and/or the formation of an impurity, and is, for example, preferably from 0.5 mol to 5.0 mol, more preferably from 0.8 mol to 2.0 mol, per mol of the 2-cyclopenten-1-ol compound (5) in view of the reactivity and/or economy.

A solvent used in the substitution reaction may be any solvent that has no adverse effect on the substitution reaction. Examples of the solvent used in the substitution reaction include halogen-based solvents such as methylene chloride, chloroform, carbon tetrachloride, and 1,2-dichloroethane; hydrocarbon solvents such as hexane, heptane, benzene, and toluene; ether solvents such as diethyl ether, tetrahydrofuran, 1,4-dioxane, and ethyleneglycol dimethyl ether; nitrile solvents such as acetonitrile; ketone solvents such as acetone, methyl ethyl ketone, and diisobutyl ketone; ester solvents such as ethyl acetate and butyl acetate; and aprotic polar solvents such as N,N-dimethylformamide, N,N-dimethylacetamide, dimethyl sulfoxide, and hexamethylphosphoric triamide. The halogen-based solvents, the ether solvents, and the aprotic polar solvents are preferred in view of the reactivity and/or the yield.

The solvent may be used either alone or in combination thereof, if necessary, and may be optionally determined while considering the type and/or the reactivity and/or the selectivity of the 2-cyclopenten-1-ol compound (5) and/or the halide.

A solvent used in the substitution reaction may be the solvent already used in the halogenation as such. The same species of solvent as in the halogenation or any solvent different from the solvent used in the halogenation may be added into the substitution reaction system to increase the reactivity and/or to adjust the concentration.

An amount of the solvent used in the substitution reaction may be optionally determined while considering the reactivity of the 2-cyclopenten-1-ol compound (5) and/or the halide and/or the formation of an impurity, and is, for example, preferably from 50 g to 10000 g, more preferably from 500 g to 8000 g, per mol of the 2-cyclopenten-1-ol compound (5) in view of the reactivity and/or the by-production of an impurity.

A reaction temperature of the substitution reaction may be optionally determined while considering the reactivity of the 2-cyclopenten-1-ol compound (5) and/or the halide and/or the formation of an impurity, and is, for example, preferably from −60° C. to 150° C., more preferably from −20° C. to 50° C., in view of the reactivity and/or the formation of an impurity.

The reaction time of the substitution reaction is preferably optimized, depending on the reactivity of the 2-cyclopenten-1-ol compound (5) and/or the halide, by monitoring the reaction progress with, for example, gas chromatography and/or thin layer chromatography to confirm the disappearance of the 2-cyclopenten-1-ol compound (5) and/or the halide. For example, the reaction time of the substitution reaction is preferably from 1 hour to 168 hours, more preferably from 1 hour to 24 hours, even more preferably 1 hour to 6 hours, in view of the yield and/or the formation of an impurity.

The haloacetaldehyde alkyl 2-cyclopentenyl acetal compound (1) formed in the substitution reaction may be suitably isolated and/or purified in any purification method used in usual organic synthesis such as distillation at a reduced pressure and/or various chromatography. Distillation at a reduced pressure is preferred in view of the industrial economy. When the haloacetaldehyde alkyl 2-cyclopentenyl acetal compound (1) formed in the substitution reaction has a sufficient purity, the crude product comprising the haloacetaldehyde alkyl 2-cyclopentenyl acetal compound (1) may be used as such without purification in a subsequent step.

B. Next, a process for preparing the (2-cyclopentenyl) acetate ester compound of the following general formula (2) will be described below.

The (2-cyclopentenyl)acetate ester compound (2) is prepared by subjecting the haloacetaldehyde alkyl 2-cyclopentenyl acetal compound (1) to a dehydrohalogenation (–HY) reaction in the presence of a base, followed by a rearrangement reaction, as shown in the following reaction formula (see, Example 2-1 to Example 2-9 below).

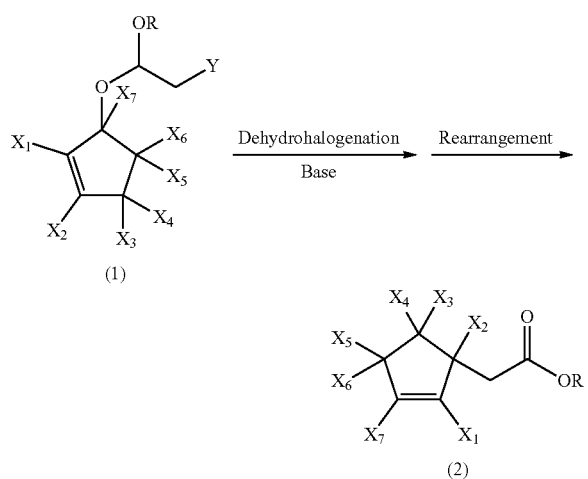

The haloacetaldehyde alkyl 2-cyclopentenyl acetal compound (1), which is a starting material, is as mentioned above. R in the general formula (1) is as defined above and is preferably a linear alkyl group having 1 to 4 carbon atoms in view of the reactivity. Linear alkyl groups having 1 to 3 carbon atoms, which are a methyl group, an ethyl group, and an n-propyl group, are more preferred in view of the reactivity and/or the availability.

Next, the (2-cyclopentenyl)acetate ester compound (2) to be formed in the rearrangement reaction will be described below.

R and $X_1$ to $X_7$ in the general formula (2) are as defined for the general formula (1). When the (2-cyclopentenyl) acetate ester compound (2) is prepared from the haloacetaldehyde alkyl 2-cyclopentenyl acetal compound (1), each of $X_1$ to $X_7$ in the general formula (2) is a hydrogen atom or a methyl group as defined for the general formula (1).

Examples of the (2-cyclopentenyl)acetate ester compound (2) include linear alkyl (monomethyl-2-cyclopentenyl)acetate esters such as methyl (1-methyl-2-cyclopentenyl)acetate, ethyl (1-methyl-2-cyclopentenyl)acetate, n-propyl (1-methyl-2-cyclopentenyl)acetate, n-butyl (1-methyl-2-cyclopentenyl)acetate, methyl (4-methyl-2-cyclopentenyl)acetate, ethyl (4-methyl-2-cyclopentenyl)acetate, n-propyl (4-methyl-2-cyclopentenyl)acetate, and n-butyl (4-methyl-2-cyclopentenyl)acetate; branched alkyl (monomethyl-2-cyclopentenyl)acetate esters such as isopropyl (1-methyl-2-cyclopentenyl)acetate, isobutyl (1-methyl-2-cyclopentenyl) acetate, isopropyl (4-methyl-2-cyclopentenyl)acetate, and isobutyl (4-methyl-2-cyclopentenyl)acetate; linear alkyl (dimethyl-2-cyclopentenyl)acetate esters such as methyl (1,2-dimethyl-2-cyclopentenyl)acetate, ethyl (1,2-dimethyl-2-cyclopentenyl)acetate, n-propyl (1,2-dimethyl-2-cyclopentenyl)acetate, n-butyl (1,2-dimethyl-2-cyclopentenyl)acetate, methyl (4,4-dimethyl-2-cyclopentenyl)acetate, ethyl (4,4-dimethyl-2-cyclopentenyl) acetate, n-propyl (4,4-dimethyl-2-cyclopentenyl)acetate, and n-butyl (4,4-dimethyl-2-cyclopentenyl)acetate; branched alkyl (dimethyl-2-cyclopentenyl)acetate esters such as isopropyl (1,2-dimethyl-2-cyclopentenyl)acetate, isobutyl (1,2-dimethyl-2-cyclopentenyl)acetate, isopropyl (4,4-dimethyl-2-cyclopentenyl)acetate, and isobutyl (4,4-dimethyl-2-cyclopentenyl)acetate; linear alkyl (trimethyl-2-cyclopentenyl)acetate esters such as methyl (1,5,5-trimethyl-2-cyclopentenyl)acetate, ethyl (1,5,5-trimethyl-2-cyclopentenyl)acetate, n-propyl (1,5,5-trimethyl-2-cyclopentenyl)acetate, n-butyl (1,5,5-trimethyl-2-cyclopentenyl)acetate, methyl (1,2,5-trimethyl-2-cyclopentenyl)acetate, ethyl (1,2,5-trimethyl-2-cyclopentenyl)acetate, n-propyl (1,2,5-trimethyl-2-cyclopentenyl)acetate, and n-butyl (1,2,5-trimethyl-2-cyclopentenyl)acetate; and branched alkyl (trimethyl-2-cyclopentenyl)acetate esters such as isopropyl (1,5,5-trimethyl-2-cyclopentenyl)acetate, isobutyl (1,5,5-trimethyl-2-cyclopentenyl)acetate, isopropyl (1,2,5-trimethyl-2-cyclopentenyl)acetate, and isobutyl (1,2,5-trimethyl-2-cyclopentenyl)acetate.

When the (2-cyclopentenyl)acetate ester compound (2) has one or more asymmetric carbon atoms in the general formula (2), the (2-cyclopentenyl)acetate ester compound (2) includes its enantiomers, diastereomers, and a mixture of such stereoisomers in the same or different amounts.

The dehydrohalogenation reaction may be carried out in the presence of a base, and may be carried out with heating or cooling, if needed.

Examples of the base used in the dehydrohalogenation reaction include metal alkoxides such as sodium methoxide, sodium ethoxide, sodium t-butoxide, lithium methoxide, lithium ethoxide, lithium t-butoxide, potassium methoxide, potassium ethoxide, and potassium t-butoxide; metal hydroxides such as sodium hydroxide, lithium hydroxide, and potassium hydroxide; organometallic reagents such as methyl lithium, ethyl lithium, n-butyl lithium, and methylmagnesium chloride; metal amides such as lithium diisopropylamide, lithium hexamethyldisilazide, sodium hexamethyldisilazide, and lithium dicyclohexylamide; and organic nitrogen compounds such as triethylamine, diisopropylethylamine, tributylamine, N,N-dimethylaniline, pyridine, 4-dimethylaminopyridine, pyrrolidine, piperidine, collidine, lutidine, morpholine, piperazine, 1,8-diazabicyclo[5.4.0]undeca-7-ene, and 1,5-diazabicyclo[4.3.0]nona-5-ene. Metal alkoxides are preferred in view of the reactivity and/or the formation of an impurity.

The base may be used either alone or in combination thereof, if necessary, and may be optionally determined while considering the type and/or the reactivity and/or the selectivity of the haloacetaldehyde alkyl 2-cyclopentenyl acetal compound (1).

An amount of the base used varies, depending on the structure and/or the reactivity of the haloacetaldehyde alkyl 2-cyclopentenyl acetal compound (1). For example, the amount is preferably from 0.2 mol to 5.0 mol, more preferably from 0.5 mol to 2.0 mol, per mol of the haloacetaldehyde alkyl 2-cyclopentenyl acetal compound (1) in view of the yield and/or the formation of an impurity.

A solvent used in the dehydrohalogenation reaction may be any solvent that has no adverse effect on the dehydrohalogenation reaction. Examples of the solvent used in the dehydrohalogenation reaction include alcoholic solvents such as methanol, ethanol, isopropyl alcohol, and t-butyl alcohol; ether solvents such as diethyl ether, di-n-butyl ether, di-t-butyl ether, tetrahydrofuran, 1,4-dioxane, and diethyleneglycol dimethyl ether; hydrocarbon solvents such as hexane, heptane, benzene, toluene, and xylene; aprotic polar solvents such as N,N-dimethylformamide, N,N-dimethylacetamide, 1,3-dimethyl-2-imidazolidinone, dimethyl sulfoxide, and hexamethylphosphoric triamide; and nitrile solvents such as acetonitrile. The ether solvents and the aprotic polar solvents are preferred in view of the reactivity.

The solvent may be used either alone or in combination thereof, if necessary, and may be optionally determined while considering the type and/or the reactivity and/or the selectivity of the haloacetaldehyde alkyl 2-cyclopentenyl acetal compound (1).

An amount of the solvent used may be optionally determined while considering the reactivity and/or solubility of the haloacetaldehyde alkyl 2-cyclopentenyl acetal compound (1), and is, for example, preferably from 30 g to 10000 g, more preferably 100 g to 5000 g, per mol of the haloacetaldehyde alkyl 2-cyclopentenyl acetal compound (1) in view of the reactivity and/or economy.

A reaction temperature of the dehydrohalogenation reaction may be optionally determined while considering the reactivity of the haloacetaldehyde alkyl 2-cyclopentenyl acetal compound (1) and/or the formation of an impurity, and is for example, preferably from −60° C. to 150° C., more preferably from −20° C. to 80° C., in view of the reactivity and/or the formation of an impurity.

The reaction time of the dehydrohalogenation reaction is preferably optimized, depending on the reactivity of the haloacetaldehyde alkyl 2-cyclopentenyl acetal compound (1), by monitoring the reaction progress with, for example, gas chromatography and/or thin layer chromatography to confirm the disappearance of the haloacetaldehyde alkyl 2-cyclopentenyl acetal compound (1) which is a substrate. For example, the reaction time of the dehydrohalogenation reaction is preferably from 1 hour to 168 hours, more preferably from 1 hour to 24 hours, even more preferably from 1 hour to 12 hours, in view of the yield and/or the formation of an impurity.

During the dehydrohalogenation reaction, an alkyl 2-cyclopentenyl ketene acetal compound of the following general formula (6) is thought to be formed in the reaction system as a product of the dehydrohalogenation reaction.

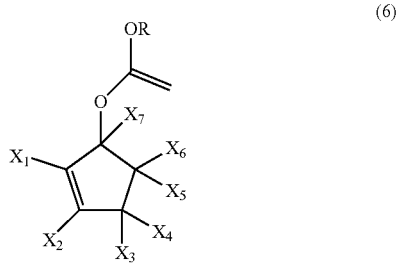

(6)

R and $X_1$ to $X_7$ in the general formula (6) are as defined for the general formula (1). When the alkyl 2-cyclopentenyl ketene acetal compound (6) is prepared from the haloacetaldehyde alkyl 2-cyclopentenyl acetal compound (1), each of $X_1$ to $X_7$ in the general formula (6) is a hydrogen atom or a methyl group as defined for the general formula (1).

The product of the dehydrohalogenation reaction may be isolated and/or purified in any purification method used in usual organic synthesis such as distillation at a reduced pressure and/or various chromatography, and then can be used in a subsequent rearrangement reaction. When the product of the dehydrohalogenation reaction is difficult to be isolated and/or purified due to its nature, the product is preferably used as such in a subsequent rearrangement reaction.

Next, in the rearrangement reaction, a (2-cyclopentenyl) acetate ester compound (2) is prepared from the product of the dehydrohalogenation reaction via a [3,3]-sigmatropic rearrangement as shown in the following reaction formula. When $X_2$ in the (2-cyclopentenyl)acetate ester compound (2) is a methyl group, the carbon atom attached to the alkoxycarbonylmethyl group becomes quaternary, resulting in greater steric hindrance of the (2-cyclopentenyl)acetate ester compound (2) and difficulty in preparation of the (2-cyclopentenyl)acetate ester compound (2) using usual anion species. Therefore, the preparation method utilizing the [3,3]-sigmatropic rearrangement is thought to be effective in the process for preparing the (2-cyclopentenyl)acetate ester compound (2).

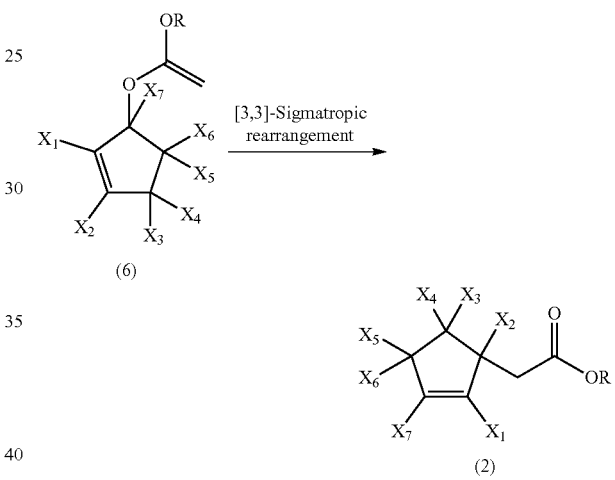

The rearrangement reaction may be carried out in a solvent or without a solvent, and may be carried out with heating or cooling, if needed.

A solvent used in the rearrangement reaction may be any solvent that has no adverse effect on the rearrangement reaction. Examples of the solvent used in the rearrangement reaction include alcoholic solvents such as methanol, ethanol, isopropyl alcohol, and t-butyl alcohol; ether solvents such as diethyl ether, di-n-butyl ether, di-t-butyl ether, tetrahydrofuran, 1,4-dioxane, and diethyleneglycol dimethyl ether; hydrocarbon solvents such as hexane, heptane, benzene, toluene, and xylene; aprotic polar solvents such as N,N-dimethylformamide, N,N-dimethylacetamide, 1,3-dimethyl-2-imidazolidinone, dimethyl sulfoxide, and hexamethylphosphoric triamide; and nitrile solvents such as acetonitrile. The ether solvents and the aprotic polar solvents are preferred in view of the reactivity.

The solvent may be used either alone or in combination thereof, if necessary, and may be optionally determined while considering the type and/or the reactivity of the product of the dehydrohalogenation reaction.

When the product of the dehydrohalogenation reaction is used in a subsequent rearrangement reaction without isolation and/or purification, a solvent to be used in the rearrangement reaction may be the solvent itself used in the dehydrohalogenation reaction. Any solvent may be additionally used in the rearrangement reaction system to adjust the reaction temperature and/or concentration.

An amount of the solvent used in the rearrangement reaction may be optionally determined while considering the reactivity and/or solubility of the product of the dehydrohalogenation reaction, which is a substrate for the rearrangement reaction. For example, an amount of the solvent used is preferably from greater than 0 g to 10000 g, more preferably 50 g to 3000 g, per mol of the haloacetaldehyde alkyl 2-cyclopentenyl acetal compound (1) or the product of the dehydrohalogenation reaction in view of the reactivity and/or economy.

A reaction temperature of the rearrangement reaction may be optionally determined while considering the reactivity of the product of the dehydrohalogenation reaction and/or the formation of an impurity, and is, for example, preferably from −60° C. to 250° C., more preferably from 0° C. to 150° C., in view of the reactivity and/or the formation of an impurity.

The reaction time of the rearrangement reaction is preferably optimized, depending on the reactivity of the product of the dehydrohalogenation reaction, by monitoring the reaction progress with, for example, gas chromatography and/or thin layer chromatography to confirm the disappearance of the product of the dehydrohalogenation reaction. For example, the reaction time of the rearrangement reaction is preferably from 1 hour to 168 hours, more preferably from 1 hour to 24 hours, even more preferably from 1 hour to 6 hours, in view of the yield and/or the formation of an impurity.

The (2-cyclopentenyl)acetate ester compound (2) formed in the rearrangement reaction may be suitably isolated and/or purified in any purification method used in usual organic synthesis such as distillation at a reduced pressure and/or various chromatography. Distillation at a reduced pressure is preferred in view of the industrial economy. When the (2-cyclopentenyl)acetate ester compound (2) formed in the rearrangement reaction has a sufficient purity, the crude product comprising the (2-cyclopentenyl)acetate ester compound (2) may be used as such without purification in a subsequent step.

C. A process for preparing the (2-cyclopentenyl)acetic acid compound of the following general formula (3) will be described below.

The (2-cyclopentenyl)acetic acid compound (3) is prepared by hydrolyzing the (2-cyclopentenyl)acetate ester compound (2) obtained in the section B, as shown in the following reaction formula (see, Example 3-1 to Example 3-5 below).

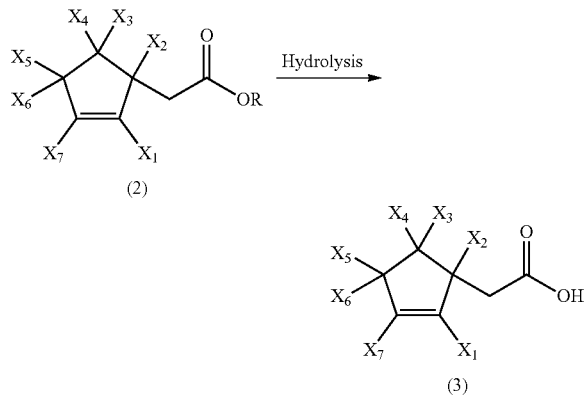

The (2-cyclopentenyl)acetate ester compound (2), which is a starting material, is as mentioned above.

Next, the (2-cyclopentenyl)acetic acid compound (3) to be formed in the hydrolysis reaction will be described below.

$X_1$ to $X_7$ in the general formula (3) are as defined for the general formula (1). When the (2-cyclopentenyl)acetic acid compound (3) is prepared from the (2-cyclopentenyl)acetate ester compound (2), each of $X_1$ to $X_7$ in the general formula (3) is a hydrogen atom or a methyl group as defined for the general formula (2).

Examples of the (2-cyclopentenyl)acetic acid compound (3) include (monomethyl-2-cyclopentenyl)acetic acids such as (1-methyl-2-cyclopentenyl)acetic acid and (4-methyl-2-cyclopentenyl)acetic acid; (dimethyl-2-cyclopentenyl)acetic acids such as (1,2-dimethyl-2-cyclopentenyl)acetic acid and (4,4-dimethyl-2-cyclopentenyl)acetic acid; and (trimethyl-2-cyclopentenyl)acetic acids such as (1,5,5-trimethyl-2-cyclopentenyl)acetic acid and (1,2,5-trimethyl-2-cyclopentenyl)acetic acid.

When the (2-cyclopentenyl)acetic acid compound (3) has one or more asymmetric carbons, the (2-cyclopentenyl)acetic acid compound (3) may be its enantiomers, diastereomers, and a mixture of such stereoisomers in the same or different amounts.

The hydrolysis reaction may be any known hydrolysis reaction, and may be carried out with heating or cooling, if needed.

The hydrolysis reaction may be carried out, for example, in a basic condition in the presence of a base, in an acidic condition in the presence of an acid, or in a neutral condition in the presence of a salt or a halogenated silane.

Examples of the base used in the hydrolysis in a basic condition include hydroxide salts such as sodium hydroxide, lithium hydroxide, potassium hydroxide, and barium hydroxide; carbonates or bicarbonates such as sodium carbonate, potassium carbonate, sodium bicarbonate, and potassium bicarbonate; and alkoxides such as sodium methoxide, sodium ethoxide, sodium t-butoxide, lithium methoxide, lithium ethoxide, lithium t-butoxide, potassium methoxide, potassium ethoxide, and potassium t-butoxide.

The base may be used either alone or in combination thereof, if necessary, and may be optionally determined while considering the type and/or the reactivity and/or the selectivity of the (2-cyclopentenyl)acetate ester compound (2).

Examples of the acid used in the hydrolysis in an acidic condition include inorganic acids such as hydrochloric acid, hydrobromic acid, sulfuric acid, and nitric acid; organic acids such as acetic acid, formic acid, oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, and titanium (IV) isopropoxide.

The acid may be used either alone or in combination thereof, if necessary, and may be optionally determined while considering the type and/or the reactivity and/or selectivity of the (2-cyclopentenyl)acetate ester compound (2).

Examples of the salt or halogenated silane used in the hydrolysis in a neutral condition include salts such as lithium iodide, lithium bromide, sodium cyanide, potassium cyanide, lithium methanethiolate, and sodium benzenethiolate; and halogenated silanes such as trimethylsilyl iodide and trimethylsilyl bromide.

The salt or halogenated silane may be used either alone or in combination thereof, if necessary, and may be optionally determined while considering the type and/or the reactivity and/or selectivity of the (2-cyclopentenyl)acetate ester compound (2).

The hydrolysis reaction is preferably carried out in a basic condition and is more preferably carried out in the presence of a hydroxide salt, a carbonate, or a bicarbonate in view of the yield and/or the formation of an impurity.

An amount of the base, acid, or salt or halogenated silane used in the hydrolysis reaction may be arbitrarily set in the range from a very low catalytic amount to a large excess, depending on the reactivity of the (2-cyclopentenyl)acetate ester compound (2), and is, for example, preferably from 0.1 mol to 50.0 mol, more preferably from 0.5 mol to 10.0 mol, per mol of the (2-cyclopentenyl)acetate ester compound (2) in view of the reaction time and/or yield.

A solvent used in the hydrolysis reaction may be any solvent that has no adverse effect on the hydrolysis reaction. Examples of the solvent used in the hydrolysis reaction include water; alcoholic solvents such as methanol, ethanol, isopropyl alcohol, and t-butyl alcohol; ether solvents such as diethyl ether, di-n-butyl ether, di-t-butyl ether, tetrahydrofuran, 1,4-dioxane, and diethyleneglycol dimethyl ether; hydrocarbon solvents such as hexane, heptane, benzene, toluene, and xylene; aprotic polar solvents such as N,N-dimethylformamide, N,N-dimethylacetamide, 1,3-dimethyl-2-imidazolidinone, dimethyl sulfoxide, and hexamethylphosphoric triamide; and nitrile solvents such as acetonitrile. The alcoholic solvents and the ether solvents are preferred in view of the reactivity.

The solvent may be used either alone or in combination thereof, if necessary, and may be optionally determined while considering the type and/or the reactivity of the (2-cyclopentenyl)acetate ester compound (2).

An amount of the solvent used may be optionally determined while considering the reactivity and/or solubility of the (2-cyclopentenyl)acetate ester compound (2), and is, for example, preferably from 30 g to 20000 g, more preferably 50 g to 8000 g, per mol of the (2-cyclopentenyl)acetate ester compound (2) in view of the reactivity and/or economy.

A reaction temperature of the hydrolysis reaction may be optionally determined while considering the reactivity of the (2-cyclopentenyl)acetate ester compound (2) and/or the formation of an impurity, and is, for example, preferably from −60° C. to 250° C., more preferably from 0° C. to 100° C., in view of the reactivity and/or the formation of an impurity.

The reaction time of the hydrolysis reaction is preferably optimized, depending on the reactivity of the (2-cyclopentenyl)acetate ester compound (2), by monitoring the reaction progress with, for example, gas chromatography and/or thin layer chromatography to confirm the disappearance of the (2-cyclopentenyl)acetate ester compound (2) which is a substrate. For example, the reaction time of the hydrolysis reaction is preferably from 1 hour to 168 hours, more preferably from 1 hour to 24 hours, even more preferably 1 hour to 12 hours, in view of the yield and/or the formation of an impurity.

The (2-cyclopentenyl)acetic acid compound (3) formed in the hydrolysis reaction may be treated by dissolving it in a basic condition to form a carboxylate salt in an aqueous layer, extracting the aqueous layer containing the carboxylate salt, layer-separating the organic layer, acidifying the resulting aqueous layer, and re-extracting the aqueous layer with an organic solvent.

The (2-cyclopentenyl)acetic acid compound (3) formed in the hydrolysis reaction may be suitably isolated and/or purified in any purification method used in usual organic synthesis such as distillation at a reduced pressure and/or various chromatography. Distillation at a reduced pressure is preferred in view of the industrial economy. When a target compound (2-cyclopentenyl)acetic acid (3) has a sufficient purity, the crude product containing the (2-cyclopentenyl)acetic acid compound (3) may be used as such without purification in a subsequent step.

Thus, it is possible to prepare efficiently and industrially the (2-cyclopentenyl)acetate ester compound (2) and the (2-cyclopentenyl)acetic acid compound (3) without an ignitable starting material and an industrially expensive starting material, in an industrially readily applicable range of a reaction temperature by subjecting the haloacetaldehyde alkyl 2-cyclopentenyl acetal compound (1) to a dehydrohalogenation reaction in the presence of a base, followed by a rearrangement reaction.

EXAMPLES

The present invention will be described with reference to the following Examples and Comparative Examples. It should be construed that the present invention is not limited to or by the Examples.

The term "purity" as used herein means an area percentage determined by gas chromatography (hereinafter referred to also as "GC"), unless otherwise specified. The term "product ratio" means a relative ratio of area percentages determined by GC.

The term "yield" is calculated from the area percentages determined by GC.

The yield was calculated by the following equation in consideration of purities (% GC) of a starting material and a product.

Yield(%)=[(mass of a product obtained in a reaction×% GC)/molecular mass of a product]÷[(mass of a starting material×% GC)/molecular mass of a starting material]}×100

GC conditions were as follows:

GC conditions for determination of "purity" and "product ratio":GC: Capillary gas chromatograph GC-2010 (Shimadzu Corporation); column: DB-5, 0.25 μm×0.25 mm>×30 m, carrier gas: He (1.55 mL/min); detector: FID; column temperature: 60° C., kept for 3 minutes, elevated by 10° C./min, up to 230° C.

As used herein, H represents a hydrogen atom, Me represents a methyl group, Et represents an ethyl group, $^n$Bu represents an n-butyl group, $^i$Pr represents an isopropyl group, and Br represents a bromine atom. In the following reaction formula, the description of $X_1$ to $X_7$ for compound (1) is omitted.

Example 1

The following Example 1-1 to Example 1-7 describe a process for preparing haloacetaldehyde alkyl 2-cyclopentenyl acetal compounds (1), as shown in the following reaction formula.

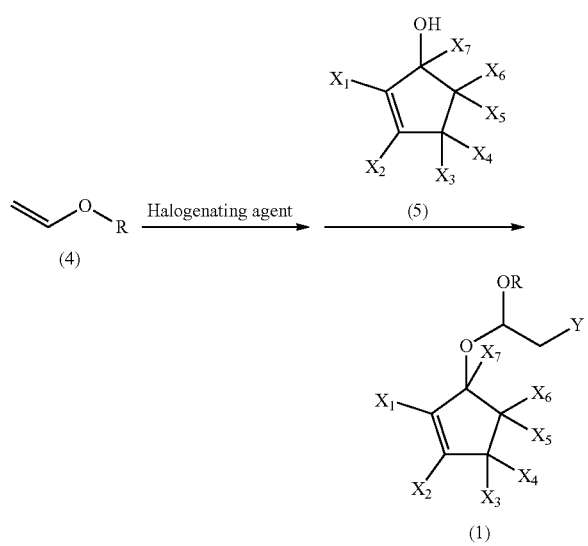

Example 1-1

Preparation of bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br)

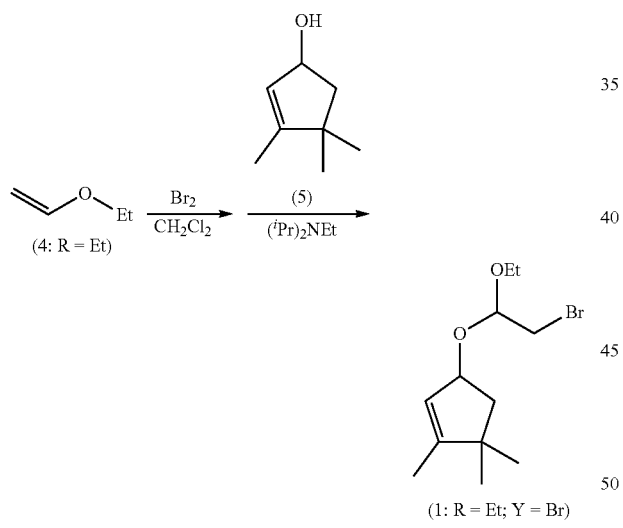

Air in a reactor equipped with a stirrer, a condenser, and a thermometer was purged with nitrogen. Then, to the reactor were added bromine ($Br_2$) (26.36 g: 0.165 mol) and methylene chloride ($CH_2Cl_2$) (750.0 g), and the liquid temperature was lowered to −5° C. to 0° C. Ethyl vinyl ether (4: R=Et) (12.98 g: 0.180 mol) was added dropwise to the mixture whose temperature was maintained at a liquid temperature of −5° C. to 0° C. over 90 minutes. After the completion of the dropwise addition, the reaction mixture was stirred at a liquid temperature of −5° C. to 0° C. for 30 minutes. After the completion of the stirring, diisopropylethylamine (($^i$Pr)$_2$NEt) (23.27 g: 0.180 mol) was added at a liquid temperature of −5° C. to 0° C. over 10 minutes. After the completion of the addition, 3,4,4-trimethyl-2-cyclopenten-1-ol (5: $X_1$, $X_5$, $X_6$, $X_7$=H; $X_2$, $X_3$, $X_4$=Me) (18.93 g: 0.150 mol, purity 94.9%) was added dropwise at liquid temperature of −10° C. to −5° C. over 1 hour. After the completion of the dropwise addition, the reaction mixture was stirred at a liquid temperature of −5° C. to 0° C. for 1 hour, and then at a liquid temperature of 20° C. to 25° C. for 3 hours.

After the stirring, an aqueous 3.5 wt % sodium bicarbonate solution (500.0 g) was added to the reaction mixture to quench the reaction. After the quenching, the reaction mixture was layer-separated into an organic layer and an aqueous layer. The resulting organic layer was washed with water (300.0 g) and with an aqueous 10.0 wt % sodium chloride solution (300.0 g) in this order. The solvent was removed from the washed organic layer at a reduced pressure, and the crude product was then purified by distillation at a reduced pressure to obtain bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br) (36.84 g: 0.133 mol, yield 88.6%, purity 91.8%).

The following are various spectrum data of bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br) thus prepared.

Nuclear magnetic resonance spectrum: $^1$H-NMR (500 MHz, $CDCl_3$): δ 1.00 (1.5H, s), 1.00 (1.5H, s), 1.10 (1.5H, s), 1.11 (1.5H, s), 1.22 (1.5H, t, J=6.9 Hz), 1.23 (1.5H, t, J=7.1 Hz), 1.66 (1.5H, t, J=1.6 Hz), 1.66 (1.5H, t, J=1.5 Hz), 1.75 (0.5H, q, J=4.4 Hz), 1.77 (0.5H, q, 4.4 Hz), 2.02 (0.5H, q, J=5.7 Hz), 2.05 (0.5H, q, J=5.7 Hz), 3.32-3.37 (m, 2H), 3.53-3.62 (1H, m), 3.63-3.73 (1H, m), 4.62-4.68 (1H, m), 4.71 (0.5H, t, J=2.9 Hz), 4.73 (0.5H, t, J=3.1 Hz), 5.35 (1H, br) ppm. $^{13}$C-NMR (126 MHz, $CDCl_3$): δ 12.29, 15.13, 15.22, 27.31, 27.35, 27.73, 27.82, 32.29, 32.42, 45.09, 45.16, 47.12, 47.99, 61.34, 61.89, 79.95, 80.02, 100.53, 101.00, 123.24, 123.58, 153.88, 153.93 ppm.

Mass spectrum EI (70 eV): m/z 152, 151, 125, 123, 93, 91, 83, 81, 79, 77, 72, 57, 43, 29.

Infrared absorption spectrum (D-ATR): ν ($cm^{-1}$) 583, 683, 829, 892, 1032, 1055, 1115, 1190, 1223, 1338, 1361, 1376, 1437, 1465, 1653, 2866, 2929, 2956, 3046.

Example 1-2

Preparation of bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br)

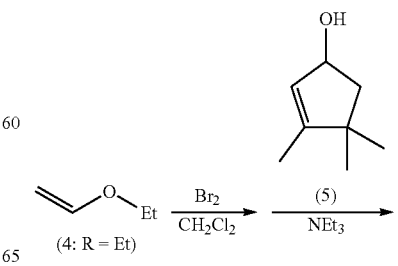

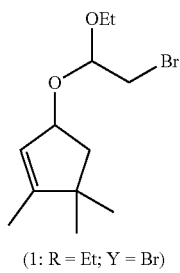

(1: R = Et; Y = Br)

The procedures of Example 1-1 were repeated with the exception that triethylamine (NEt$_3$) (18.21 g: 0.180 mol) was used instead of diisopropylethylamine (($^i$Pr)$_2$NEt) as a base, so that obtained was bromoacetaldehyde ethyl 3,4,4-trimethyl-2-cyclopentenyl acetal (1: R=Et; X$_1$, X$_5$, X$_6$, X$_7$=H; X$_2$, X$_3$, X$_4$=Me; Y=Br) (30.60 g: 0.110 mol, yield 73.3%, purity 89.2%).

Various spectrum data of bromoacetaldehyde ethyl 3,4,4-trimethyl-2-cyclopentenyl acetal (1: R=Et; X$_1$, X$_5$, X$_6$, X$_7$=H; X$_2$, X$_3$, X$_4$=Me; Y=Br) thus prepared were the same as those determined in Example 1-1.

Example 1-3

Preparation of bromoacetaldehyde isopropyl 3,4,4-trimethyl-2-cyclopentenyl acetal (1: R=$^i$Pr; X$_1$, X$_5$, X$_6$, X$_7$=H; X$_2$, X$_3$, X$_4$=Me; Y=Br)

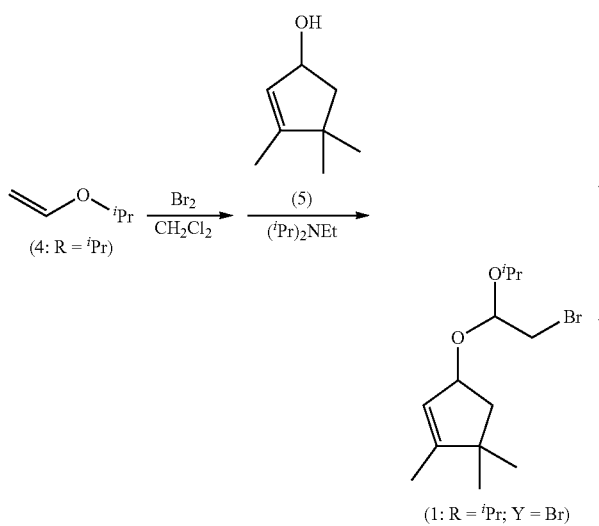

The procedures of Example 1-1 were repeated with the exception that isopropyl vinyl ether (4: R=$^i$Pr) (15.50 g: 0.180 mol) was used instead of ethyl vinyl ether (4: R=Et), so that obtained was bromoacetaldehyde isopropyl 3,4,4-trimethyl-2-cyclopentenyl acetal (1: R=$^i$Pr; X$_1$, X$_5$, X$_6$, X$_7$=H; X$_2$, X$_3$, X$_4$=Me; Y=Br) (41.19 g: 0.141 mol, yield 94.3%, purity 87.8%).

The following are various spectrum data of bromoacetaldehyde isopropyl 3,4,4-trimethyl-2-cyclopentenyl acetal (1: R=$^i$Pr; X$_1$, X$_5$, X$_6$, X$_7$=H; X$_2$, X$_3$, X$_4$=Me; Y=Br) thus prepared.

Nuclear magnetic resonance spectrum: $^1$H-NMR (500 MHz, CDCl$_3$): δ 0.97 (1.5H, s), 0.97 (1.5H, s), 1.05 (1.5H, s), 1.05 (1.5H, s), 1.10 (3H, d, J=6.0 Hz), 1.12 (3H, dd, J=6.3, 3.0 Hz), 1.62-1.65 (4H, m), 1.97 (0.5H, dd, J=13.2, 7.0 Hz), 2.02 (0.5H, dd, J=13.2, 7.0 Hz), 3.35-3.41 (2H, m), 3.82-3.86 (1H, m), 4.62 (1H, m), 4.69 (0.5H, t, J=5.1 Hz), 4.71 (0.5H, t, J=5.1), 5.35 (1H, d, 22.8 Hz) ppm. $^{13}$C-NMR (126 MHz, CDCl$_3$): δ 11.97, 12.02, 22.14, 22.35, 23.02, 23.06, 26.97, 27.57, 27.58, 34.00, 34.04, 44.51, 44.59, 46.96, 47.69, 68.39, 68.51, 78.23, 78.24, 98.62, 98.78, 123.96, 124.25, 152.10, 152.13 ppm.

Mass spectrum EI (70 eV): m/z 168, 167, 151, 125, 110, 109, 93, 91, 77, 58, 43, 27.

Infrared absorption spectrum (D-ATR): ν (cm$^{-1}$) 681, 829, 1026, 1124, 1171, 1202, 1337, 1380, 1421, 1437, 1466, 2867, 2929, 2969, 3045.

Example 1-4

Preparation of bromoacetaldehyde n-butyl 3,4,4-trimethyl-2-cyclopentenyl acetal (1: R=$^n$Bu; X$_1$, X$_5$, X$_6$, X$_7$=H; X$_2$, X$_3$, X$_4$=Me; Y=Br)

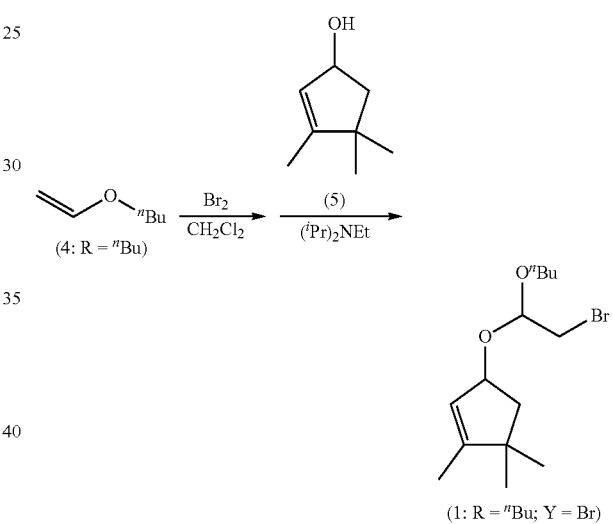

The procedures of Example 1-1 were repeated with the exception that n-butyl vinyl ether (4: R=$^n$Bu) (18.03 g: 0.180 mol) was used instead of ethyl vinyl ether (4:R=Et), so that obtained was bromoacetaldehyde n-butyl 3,4,4-trimethyl-2-cyclopentenyl acetal (1: R=$^n$Bu; X$_1$, X$_5$, X$_6$, X$_7$=H; X$_2$, X$_3$, X$_4$=Me; Y=Br) (34.62 g: 0.113 mol, yield 75.6%, purity 84.0%).

The following are various spectrum data of bromoacetaldehyde n-butyl 3,4,4-trimethyl-2-cyclopentenyl acetal (1: R=$^n$Bu; X$_1$, X$_5$, X$_6$, X$_7$=H; X$_2$, X$_3$, X$_4$=Me; Y=Br) thus prepared.

Nuclear magnetic resonance spectrum: $^1$H-NMR (500 MHz, CDCl$_3$): δ 0.88 (3H, t, J=7.5 Hz), 0.97 (3H, s), 1.05 (3H, s), 1.34 (2H, sextd, J=7.5, 2.4 Hz), 1.46-1.51 (2H, m), 1.63-1.66 (4H, m), 1.98 (0.5H, q, J=6.6 Hz), 2.01 (0.5H, q, J=6.6 Hz), 3.39-3.47 (3H, m), 3.50-3.57 (1H, m), 4.60-4.62 (1H, m), 4.67 (1H, q, J=5.6 Hz), 5.33 (0.5H, t, J=1.5 Hz), 5.37 (0.5H, t, J=1.5 Hz) ppm. $^{13}$C-NMR (126 MHz, CDCl$_3$): δ 11.97, 12.02, 13.69, 18.78, 26.95, 27.56, 31.29, 31.31, 33.25, 33.29, 44.51, 44.59, 46.87, 47.55, 65.03, 65.45, 79.11, 79.21, 99.94, 100.23, 123.82, 124.22, 152.20, 152.31 ppm.

Mass spectrum EI (70 eV): m/z 181, 179, 151, 125, 109, 93, 91, 77, 57, 41.

Infrared absorption spectrum (D-ATR): ν (cm$^{-1}$) 684, 829, 1036, 1114, 1187, 1224, 1338, 1360, 1377, 1435, 1465, 1653, 2869, 2933, 2957, 3047.

Example 1-5

Preparation of bromoacetaldehyde 2,3-dimethyl-2-cyclopentenyl ethyl acetal (1: R=Et; $X_3$, $X_4$, $X_5$, $X_6$, $X_7$=H; $X_1$, $X_2$=Me; Y=Br)

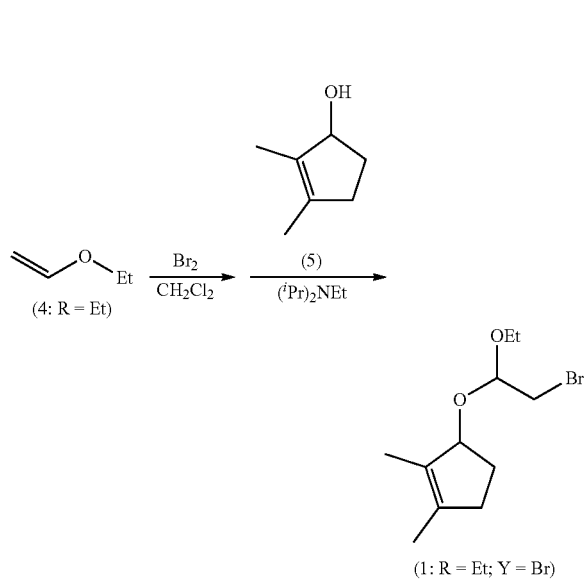

(1: R = Et; Y = Br)

The procedures of Example 1-1 were repeated with the exception that 2,3-dimethyl-2-cyclopenten-1-ol (5: $X_3$, $X_4$, $X_5$, $X_6$, $X_7$=H; $X_1$, $X_2$=Me) (16.83 g: 0.150 mol, purity 93.6%) was used instead of 3,4,4-trimethyl-2-cyclopenten-1-ol (5: $X_1$, $X_5$, $X_6$, $X_7$=H; $X_2$, $X_3$, $X_4$=Me) as a reaction substrate, so that obtained was bromoacetaldehyde 2,3-dimethyl-2-cyclopentenyl ethyl acetal (1: R=Et; $X_3$, $X_4$, $X_5$, $X_6$, $X_7$=H; $X_1$, $X_2$=Me; Y=Br) (33.79 g: 0.128 mol, yield 85.3%, purity 87.8%).

The following are various spectrum data of bromoacetaldehyde 2,3-dimethyl-2-cyclopentenyl ethyl acetal (1: R=Et; $X_3$, $X_4$, $X_5$, $X_6$, $X_7$=H; $X_1$, $X_2$=Me; Y=Br) thus prepared.

Nuclear magnetic resonance spectrum: $^1$H-NMR (500 MHz, CDCl$_3$): δ 1.12 (1.5H, t, J=7.2 Hz), 1.14 (1.5H, t, J=6.9 Hz), 1.60-1.62 (6H, m), 1.63-1.70 (1H, m), 2.03-2.15 (2H, m), 2.30 (1H, br), 3.41-3.49 (2H, m), 3.51-3.65 (2H, m), 4.47 (0.5H, br), 4.55 (0.5H, br), 4.68 (0.5H, t, J=5.4 Hz), 4.70 (0.5H, t, J=5.4 Hz) ppm. $^{13}$C-NMR (126 MHz, CDCl$_3$): δ 11.30, 11.31, 13.95, 15.15, 15.23, 28.91, 29.87, 33.36, 33.46, 35.07, 35.18, 60.78, 61.32, 85.30, 86.78, 99.53, 101.37, 130.83, 131.33, 135.27, 135.81 ppm.

Mass spectrum EI (70 eV): m/z 152, 149, 137, 123, 121, 111, 95, 94, 79, 72, 55, 42, 29.

Infrared absorption spectrum (D-ATR): ν (cm$^{-1}$) 683, 1031, 1056, 1113, 1185, 1336, 1381, 1422, 1442, 2849, 2913, 2974.

Example 1-6

Preparation of bromoacetaldehyde 5,5-dimethyl-2-cyclopentenyl ethyl acetal (1: R=Et; $X_1$, $X_2$, $X_3$, $X_4$, $X_7$=H; $X_5$, $X_6$=Me; Y=Br)

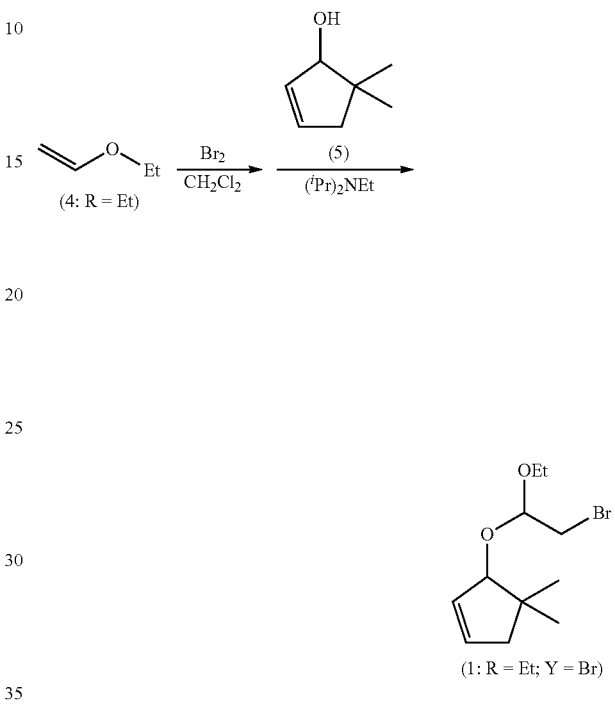

(1: R = Et; Y = Br)

The procedures of Example 1-1 were repeated with the exception that 5,5-dimethyl-2-cyclopenten-1-ol (5: $X_1$, $X_2$, $X_3$, $X_4$, $X_7$=H; $X_5$, $X_6$=Me) (16.83 g: 0.150 mol, purity 82.3%) was used instead of 3,4,4-trimethyl-2-cyclopenten-1-ol (5: $X_1$, $X_5$, $X_6$, $X_7$=H; $X_2$, $X_3$, $X_4$=Me) as a reaction substrate, so that obtained was bromoacetaldehyde 5,5-dimethyl-2-cyclopentenyl ethyl acetal (1: R=Et; $X_1$, $X_2$, $X_3$, $X_4$, $X_7$=H; $X_5$, $X_6$=Me; Y=Br) (36.28 g: 0.138 mol, yield 91.9%, purity 80.8%).

The following are various spectrum data of bromoacetaldehyde 5,5-dimethyl-2-cyclopentenyl ethyl acetal (1: R=Et; $X_1$, $X_2$, $X_3$, $X_4$, $X_7$=H; $X_5$, $X_6$=Me; Y=Br) thus prepared.

Nuclear magnetic resonance spectrum: $^1$H-NMR (600 MHz, CDCl$_3$): δ 1.07 (1.5H, s), 1.08 (1.5H, s), 1.24 (1.5H, t, J=5.1 Hz), 1.25 (1.5H, t, J=7.2 Hz), 2.04-2.06 (0.5H, m), 2.07-2.09 (0.5H, m), 2.23 (0.5H, quin, J=2.4 Hz), 2.26 (0.5H, quin, J=1.8 Hz), 3.33-3.40 (2H, m), 3.56-3.74 (2H, m), 4.17 (1H, d, J=12.6 Hz), 4.74-4.77 (1H, m), 5.72 (0.5H, dd, J=6.3, 4.2 Hz), 5.75 (0.5H, dd, J=5.8, 3.9 Hz), 5.89-5.92 (1H, m) ppm. $^{13}$C-NMR (150 MHz, CDCl$_3$): δ 15.36, 23.24, 23.33, 28.71, 29.02, 32.11, 32.49, 41.96, 42.16, 46.78, 46.82, 61.18, 62.01, 88.54, 90.52, 101.02, 102.44, 130.12, 131.02, 134.37, 134.85 ppm.

Mass spectrum EI (70 eV): m/z 153, 151, 125, 123, 81, 79, 55, 41.

Infrared absorption spectrum (D-ATR): ν (cm$^{-1}$) 684, 1031, 1056, 1125, 1190, 1346, 1364, 1422, 1444, 1467, 2870, 2901, 2929, 2958, 2975.

Example 1-7

Preparation of bromoacetaldehyde ethyl 3-methyl-2-cyclopentenyl acetal (1:R=Et; $X_1$, $X_3$, $X_4$, $X_5$, $X_6$, $X_7$=H; $X_2$=Me; Y=Br)

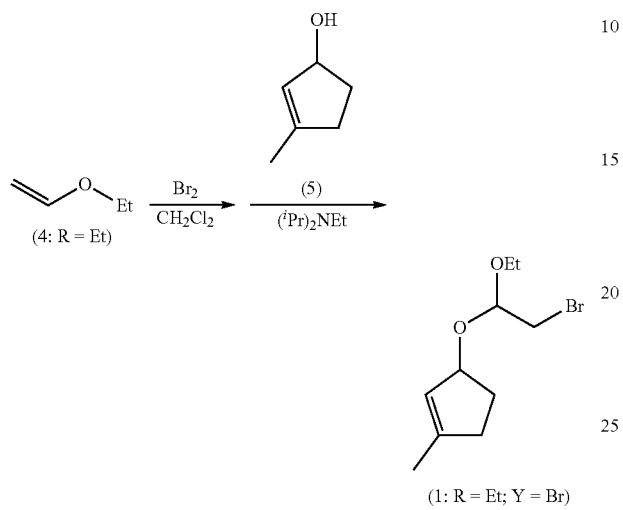

The procedures of Example 1-1 were repeated with the exception that 3-methyl-2-cyclopenten-1-ol (5: $X_1$, $X_3$, $X_4$, $X_5$, $X_6$, $X_7$=H; $X_2$=Me) (14.72 g: 0.150 mol, purity 93.6%) was used instead of 3,4,4-trimethyl-2-cyclopenten-1-ol (5: $X_1$, $X_5$, $X_6$, $X_7$=H; $X_2$, $X_3$, $X_4$=Me) as a reaction substrate, so that obtained was bromoacetaldehyde ethyl 3-methyl-2-cyclopentenyl acetal (1: R=Et; $X_1$, $X_3$, $X_4$, $X_5$, $X_6$, $X_7$=H; $X_2$=Me; Y=Br) (27.28 g: 0.110 mol, yield 73.3%, purity 89.9%).

The following are various spectrum data of bromoacetaldehyde ethyl 3-methyl-2-cyclopentenyl acetal (1: R=Et; $X_1$, $X_3$, $X_4$, $X_5$, $X_6$, $X_7$=H; $X_2$=Me; Y=Br) thus prepared.

Nuclear magnetic resonance spectrum: $^1$H-NMR (500 MHz, CDCl$_3$): δ 1.12 (1.5H, t, 6.9 Hz), 1.12 (1.5H, t, 7.2 Hz), 1.70-1.77 (4H, m), 2.70-2.13 (1H, br m), 2.13-2.22 (1H, m), 2.28-2.45 (1H, br m), 3.39-3.46 (2H, m), 3.48-3.53 (1H, m), 3.56-3.63 (1H, m), 4.68 (0.5H, t, J=4.8 Hz), 4.69 (0.5H, t, J=4.8 Hz), 4.72 (1H, br m), 5.42 (0.5H, br t, J=1.8 Hz), 5.46 (0.5H, br t, J=1.8 Hz) ppm. $^{13}$C-NMR (126 MHz, CDCl$_3$): δ 15.13, 15.16, 16.51, 16.55, 30.88, 31.36, 33.39, 34.55, 34.71, 61.05, 82.41, 82.52, 99.87, 100.14 125.28, 125.63, 145.13, 145.18 ppm.

Mass spectrum EI (70 eV): m/z 153, 151, 125, 123, 81.

Infrared absorption spectrum (D-ATR): ν (cm$^{-1}$) 681, 826, 996, 1029, 1111, 1154, 1190, 1342, 1378, 1444, 1658, 2913, 2932, 2974.

Example 2

The following Example 2-1 to Example 2-9 describe a process for preparing (2-cyclopentenyl)acetate ester compounds (2), as shown in the following reaction formula:

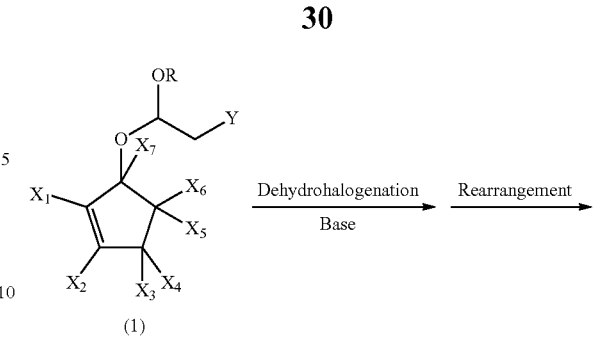

Example 2-1

Preparation of ethyl (1,5,5-trimethyl-2-cyclopentenyl)acetate (2: R=Et; $X_1$, $X_5$, $X_6$, $X_7$=H; $X_2$, $X_3$, $X_4$=Me)

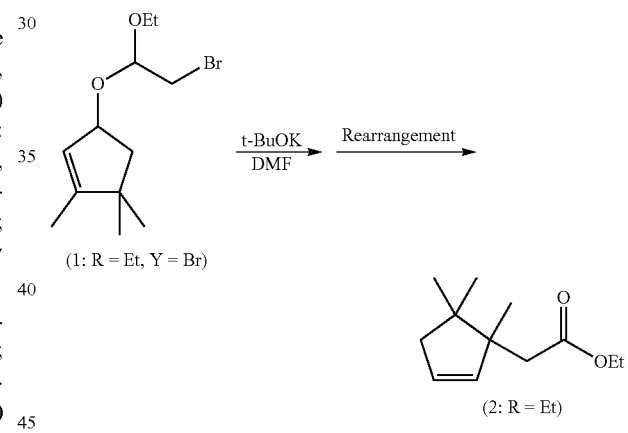

Air in a reactor equipped with a stirrer, a condenser, and a thermometer was purged with nitrogen. Then, to the reactor were added bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br) (27.72 g: 0.100 mol, purity 92.0%) obtained according to Example 1-1 and N,N-dimethylformamide (DMF) (280.0 g) and then cooled to a liquid temperature of 0° C. to 5° C. Potassium t-butoxide (t-BuOK) (12.34 g: 0.110 mol) was added to the mixture whose temperature was maintained at a liquid temperature of 0° C. to 5° C. over 30 minutes. After the completion of the addition, the reaction was allowed at a liquid temperature of 20 to 25° C. for 4 hours.

After the reaction, the reaction mixture was heated to 100° C. and stirred for 5 hours. After the completion of the stirring, the reaction mixture was cooled to 0° C. to 5° C., and water (250.0 g) was added to the reactor to quench the reaction. Diethyl ether (300.0 g) was further added to the reactor to extract and layer-separate the mixture into an organic layer and an aqueous layer. The organic layer was washed with an aqueous 10 wt % sodium chloride solution (300.0 g). The solvent was removed from the washed organic layer at a reduced pressure, and the crude product was then purified by silica gel column chromatography to obtain ethyl (1,5,5-trimethyl-2-cyclopentenyl)acetate (2: R=Et; $X_1$, $X_5$, $X_6$, $X_7$=H; $X_2$, $X_3$, $X_4$=Me) (9.76 g: 0.050 mol, yield 49.7%, purity 82.2%).

The following are various spectrum data of ethyl (1,5,5-trimethyl-2-cyclopentenyl)acetate (2: R=Et; $X_1$, $X_5$, $X_6$, $X_7$=H; $X_2$, $X_3$, $X_4$=Me) thus prepared.

Nuclear magnetic resonance spectrum: $^1$H-NMR (500 MHz, $CDCl_3$): δ 0.92 (3H, s), 0.96 (3H, s), 0.96 (3H, s), 1.25 (3H, t, J=7.3 Hz), 2.09 (1H, dt, J=15.7, 2.1 Hz), 2.16 (1H, dt, J=16.1, 2.2 Hz), 2.18 (1H, d, J=13.4 Hz), 2.31 (1H, d, J=13.4 Hz), 4.11 (2H, q, J=7.1 Hz), 5.62 (1H, dt, J=5.7, 2.4 Hz), 5.77 (1H, dt, J=5.7, 1.9 Hz) ppm. $^{13}$C-NMR (126 MHz, $CDCl_3$): δ 14.27, 19.79, 23.95, 24.47, 40.78, 44.04, 46.64, 49.81, 59.97, 127.77, 138.79, 173.07 ppm.

Mass spectrum EI (70 eV): m/z 196 ($M^+$), 181, 167, 150, 135, 122, 109, 108, 107, 93, 91, 81, 79, 77, 67, 55, 41, 28.

Infrared absorption spectrum (D-ATR): ν ($cm^{-1}$) 716, 742, 956, 1034, 1131, 1187, 1213, 1294, 1336, 1367, 1448, 1463, 1734, 2843, 2872, 2968, 2052.

Example 2-2

Preparation of ethyl (1,5,5-trimethyl-2-cyclopentenyl)acetate (2: R=Et; $X_1$, $X_5$, $X_6$, $X_7$=H; $X_2$, $X_3$, $X_4$=Me)

The procedures of Example 2-1 were repeated with the exception that after the completion of the reactions of Example 2-1, the reaction mixture was heated to 140° C. instead of 100° C. and stirred for 8 hours instead of 5 hours, so that obtained was ethyl (1,5,5-trimethyl-2-cyclopentenyl) acetate (2: R=Et; $X_1$, $X_5$, $X_6$, $X_7$=H; $X_2$, $X_3$, $X_4$=Me) (9.38 g: 0.048 mol, yield 47.8%, purity 80.0%).

The various spectrum data of ethyl (1,5,5-trimethyl-2-cyclopentenyl)acetate (2: R=Et; $X_1$, $X_5$, $X_6$, $X_7$=H; $X_2$, $X_3$, $X_4$=Me) thus prepared were the same as those determined in Example 2-1.

Example 2-3

Preparation of ethyl (1,5,5-trimethyl-2-cyclopentenyl)acetate (2: R=Et; $X_1$, $X_5$, $X_6$, $X_7$=H; $X_2$, $X_3$, $X_4$=Me)

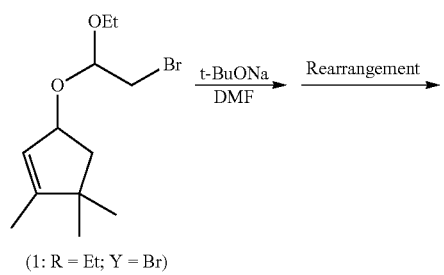

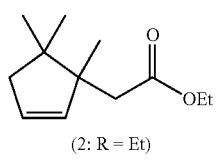

The procedures of Example 2-1 were repeated with the exception that sodium t-butoxide (t-BuONa) (10.57 g: 0.110 mol) was used instead of potassium t-butoxide (t-BuOK) as a base used in Example 2-1, so that obtained was ethyl (1,5,5-trimethyl-2-cyclopentenyl)acetate (2: R=Et; $X_1$, $X_5$, $X_6$, $X_7$=H; $X_2$, $X_3$, $X_4$=Me) (8.62 g: 0.044 mol, yield 43.9%, purity 83.7%).

The various spectrum data of ethyl (1,5,5-trimethyl-2-cyclopentenyl)acetate (2: R=Et; $X_1$, $X_5$, $X_6$, $X_7$=H; $X_2$, $X_3$, $X_4$=Me) thus prepared were the same as those determined in Example 2-1.

Example 2-4

Preparation of ethyl (1,5,5-trimethyl-2-cyclopentenyl)acetate (2: R=Et; $X_1$, $X_5$, $X_6$, $X_7$=H; $X_2$, $X_3$, $X_4$=Me)

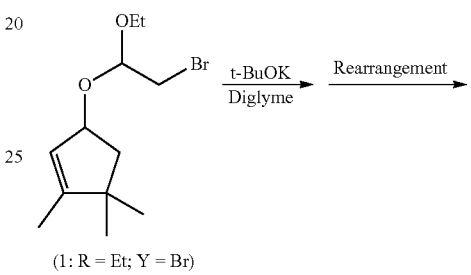

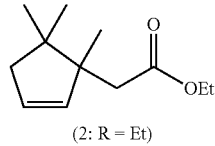

The procedures of Example 2-1 were repeated with the exception that diethyleneglycol dimethyl ether (Diglyme) (280.0 g) was used instead of N,N-dimethylformamide (DMF) as a solvent used in Example 2-1, so that obtained was ethyl (1,5,5-trimethyl-2-cyclopentenyl)acetate (2: R=Et; $X_1$, $X_5$, $X_6$, $X_7$=H; $X_2$, $X_3$, $X_4$=Me) (9.50 g: 0.048 mol, yield 48.4%, purity 84.0%).

The various spectrum data of ethyl (1,5,5-trimethyl-2-cyclopentenyl)acetate (2: R=Et; $X_1$, $X_5$, $X_6$, $X_7$=H; $X_2$, $X_3$, $X_4$=Me) thus prepared were the same as those determined in Example 2-1.

Example 2-5

Preparation of isopropyl (1,5,5-trimethyl-2-cyclopentenyl)acetate (2: R=$^i$Pr; $X_1$, $X_5$, $X_6$, $X_7$=H; $X_2$, $X_3$, $X_4$=Me)

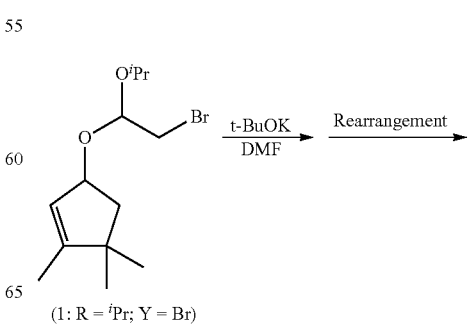

-continued

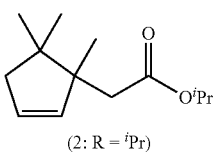

(2: R = $^i$Pr)

The procedures of Example 2-1 were repeated with the exception that bromoacetaldehyde isopropyl 3,4,4-trimethyl-2-cyclopentenyl acetal (1: R=$^i$Pr; $X_1$, $X_5$, $X_6$, $X_7$=H; $X_2$, $X_3$, $X_4$=Me; Y=Br) (29.12 g: 0.100 mol, purity 95.0%) obtained according to Example 1-3 was used instead of bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br) as a reaction substrate used in Example 2-1, and that distillation at a reduced pressure was used instead of purification by silica gel column chromatography in Example 2-1, so that obtained was isopropyl (1,5,5-trimethyl-2-cyclopentenyl)acetate (2: R=$^i$Pr; $X_1$, $X_5$, $X_6$, $X_7$=H; $X_2$, $X_3$, $X_4$=Me) (6.37 g: 0.030 mol, yield 30.3%, purity 84.5%).

The following are various spectrum data of isopropyl (1,5,5-trimethyl-2-cyclopentenyl)acetate (2: R=$^1$Pr; $X_1$, $X_5$, $X_6$, $X_7$=H; $X_2$, $X_3$, $X_4$=Me) thus prepared.

Nuclear magnetic resonance spectrum: $^1$H-NMR (500 MHz, CDCl$_3$): δ 0.93 (3H, s), 0.97 (6H, s), 1.24 (6H, d, 6.0 Hz), 2.09 (1H, dt, J=16.0, 1.8 Hz), 2.15-2.19 (2H, m), 2.29 (1H, d, 13.2 Hz), 5.01 (1H, sep, J=6.6 Hz), 5.63 (1H, dt, J=5.7, 2.4 Hz), 5.79 (1H, dt, J=6.0, 1.8 Hz) ppm. $^{13}$C-NMR (126 MHz, CDCl$_3$): δ 19.98, 22.03, 22.05, 24.05, 24.72, 41.22, 44.22, 46.79, 50.03, 67.43, 127.86, 139.00, 172.80 ppm.

Mass spectrum EI (70 eV): m/z 210 (M$^+$), 167, 153, 135, 121, 109, 108, 107, 93, 91, 81, 67, 55, 43, 27.

Infrared absorption spectrum (D-ATR): ν (cm$^{-1}$) 716, 741, 964, 1108, 1182, 1215, 1278, 1293, 1319, 1374, 1386, 1450, 1468, 1687, 1730, 2874, 2935, 2974, 3053.

Example 2-6

Preparation of n-butyl (1,5,5-trimethyl-2-cyclopentenyl)acetate (2: R=$^n$Bu; $X_1$, $X_5$, $X_6$, $X_7$=H; $X_2$, $X_3$, $X_4$=Me)

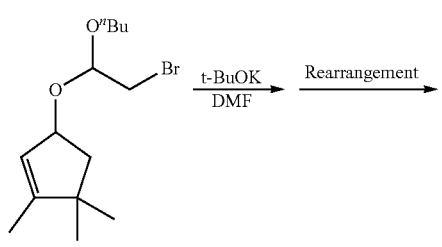

(1: R = $^n$Bu; Y = Br)

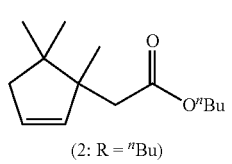

(2: R = $^n$Bu)

The procedures of Example 2-1 were repeated with the exception that bromoacetaldehyde n-butyl 3,4,4-trimethyl-2-cyclopentenyl acetal (1: R=$^n$Bu; $X_1$, $X_5$, $X_6$, $X_7$=H; $X_2$, $X_3$, $X_4$=Me; Y=Br) (30.53 g: 0.100 mol, purity 84.0%) obtained in Example 1-4 was used instead of bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br) as a reaction substrate used in Example 2-1, and that the resulting crude product was purified by distillation at a reduced pressure instead of silica gel chromatography used in Example 2-1, so that obtained was n-butyl (1,5,5-trimethyl-2-cyclopentenyl)acetate (2: R=$^n$Bu; $X_1$, $X_5$, $X_6$, $X_7$=H; $X_2$, $X_3$, $X_4$=Me) (4.98 g: 0.022 mol, yield 22.2%, purity 64.5%).

The following are various spectrum data of n-butyl (1,5,5-trimethyl-2-cyclopentenyl)acetate (2: R=$^n$Bu; $X_1$, $X_5$, $X_6$, $X_7$=H; $X_2$, $X_3$, $X_4$=Me) thus prepared.

Nuclear magnetic resonance spectrum: $^1$H-NMR (500 MHz, CDCl$_3$): δ 0.93-0.95 (6H, m), 0.97 (6H, s), 1.35-1.42 (3H, m), 1.61 (3H, quin, J=7.4 Hz), 2.05 (1H, d, J=15.6 Hz), 2.16-2.21 (2H, m), 2.32 (1H, d, J=13.2 Hz), 4.06 (2H, t, J=6.6 Hz), 5.64 (1H, dt, J=5.7, 2.6 Hz), 5.78 (1H, d, J=6.0 Hz) ppm. $^{13}$C-NMR (126 MHz, CDCl$_3$): δ 13.85, 19.37, 20.00, 24.11, 24.65, 30.85, 41.00, 44.21, 46.81, 49.98, 64.17, 127.96, 138.96, 173.41 ppm.

Mass spectrum EI (70 eV): m/z 224 (M$^+$), 209, 167, 153, 135, 122, 109, 108, 107, 93, 81, 67, 55, 41, 29.

Infrared absorption spectrum (D-ATR): ν (cm$^{-1}$) 716, 965, 1023, 1072, 1131, 1186, 1212, 1277, 1293, 1341, 1365, 1373, 1468, 1734, 2873, 2934, 2960, 3053.

Example 2-7

Preparation of ethyl (1,2-dimethyl-2-cyclopentenyl)acetate (2: R=Et; $X_3$, $X_4$, $X_5$, $X_6$, $X_7$=H; $X_1$, $X_2$=Me)

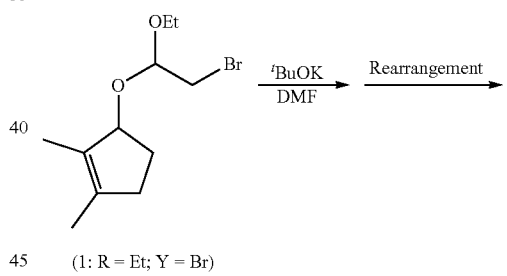

(1: R = Et; Y = Br)

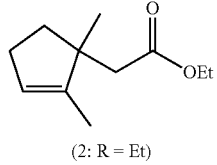

(2: R = Et)

The procedures of Example 2-1 were repeated with the exception that bromoacetaldehyde 2,3-dimethyl-2-cyclopentenyl ethyl acetal (1: R=Et; $X_3$, $X_4$, $X_5$, $X_6$, $X_7$=H; $X_1$, $X_2$=Me; Y=Br) (26.32 g: 0.100 mol, purity 87.9%) obtained according to Example 1-5 was used instead of bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br) as a reaction substrate used in Example 2-1, and that the resulting crude product was purified by distillation at a reduced pressure instead of silica gel chromatography used in Example 2-1, so that obtained was ethyl (1,2-dimethyl-2-cyclopentenyl)acetate (2: R=Et; $X_3$, $X_4$, $X_5$, $X_6$, $X_7$=H; $X_1$, $X_2$=Me) (15.13 g: 0.083 mol, yield 83.0%, purity 97.3%).

The following are various spectrum data of ethyl (1,2-dimethyl-2-cyclopentenyl)acetate (2: R=Et; $X_3$, $X_4$, $X_5$, $X_6$, $X_7$=H; $X_1$, $X_2$=Me) thus prepared.

Nuclear magnetic resonance spectrum: $^1$H-NMR (500 MHz, CDCl$_3$): δ 1.09 (3H, s), 1.24 (3H, t, J=7.2 Hz), 1.63 (3H, q, J=1.6 Hz), 1.67-1.72 (1H, m), 2.1-2.15 (1H, m), 2.17-2.21 (2H, m), 2.21 (1H, d, J=13.2 Hz), 2.33 (1H, d, J=13.2), 4.05-4.14 (2H, m), 5.29 (1H, br s, J=1.2 Hz) ppm. $^{13}$C-NMR (126 MHz, CDCl$_3$): δ 12.49, 14.40, 25.08, 29.32, 37.12, 43.59, 48.59, 60.12, 124.71, 145.56, 172.53 ppm.

Mass spectrum EI (70 eV): m/z 182 (M$^+$), 136, 94, 92, 78, 77, 67, 55, 53, 41, 39, 29.

Infrared absorption spectrum (D-ATR): ν (cm$^{-1}$) 799, 1036, 1096, 1129, 1171, 1216, 1284, 1315, 1367, 1446, 1733, 2852, 2934, 2961, 3039.

Example 2-8

Preparation of ethyl (4,4-dimethyl-2-cyclopentenyl)acetate (2: R=Et; $X_1$, $X_2$, $X_3$, $X_4$, $X_7$=H; $X_5$, $X_6$=Me)

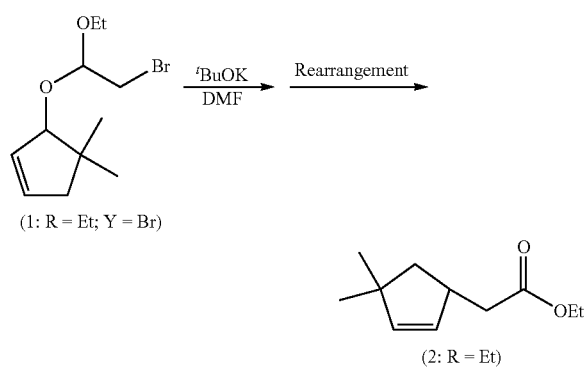

The procedures of Example 2-1 were repeated with the exception that bromoacetaldehyde 5,5-dimethyl-2-cyclopentenyl ethyl acetal (1: R=Et; $X_1$, $X_2$, $X_3$, $X_4$, $X_7$=H; $X_5$, $X_6$=Me; Y=Br) (26.32 g: 0.100 mol, purity 97.7%) obtained according to Example 1-6 was used instead of bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br) as a reaction substrate used in Example 2-1, and that the resulting crude product was purified by distillation at a reduced pressure instead of silica gel chromatography used in Example 2-1, so that obtained was ethyl (4,4-dimethyl-2-cyclopentenyl)acetate (2: R=Et; $X_1$, $X_2$, $X_3$, $X_4$, $X_7$=H; $X_5$, $X_6$=Me) (14.91 g: 0.082 mol, yield 81.8%, purity 81.0%).

The following are various spectrum data of ethyl (4,4-dimethyl-2-cyclopentenyl)acetate (2: R=Et; $X_1$, $X_2$, $X_3$, $X_4$, $X_7$=H; $X_5$, $X_6$=Me) thus prepared.

Nuclear magnetic resonance spectrum: $^1$H-NMR (600 MHz, CDCl$_3$): δ 1.03 (3H, s), 1.09 (3H, s), 1.25-1.29 (4H, m), 1.96 (1H, dd, J=12.6, 7.8 Hz), 2.29 (1H, dd, J=15.0, 8.4 Hz), 2.40 (1H, dd, J=12.0.6.3 Hz), 3.16 (1H, quin, J=7.5 Hz), 4.14 (2H, q, J=3.8 Hz), 5.48 (1H, d, J=5.4 Hz), 5.54 (1H, d, J=5.5 Hz) ppm. $^{13}$C-NMR (150 MHz, CDCl$_3$): δ 14.43, 28.49, 29.98, 41.24, 41.83, 45.37, 45.79, 60.34, 130.84, 142.45, 173.07 ppm.

Mass spectrum EI (70 eV): m/z 182 (M$^+$), 167, 153, 137, 121, 107, 95, 93, 79, 77, 67, 55, 41, 28.

Infrared absorption spectrum (D-ATR): ν (cm$^{-1}$) 757, 1031, 1167, 1259, 1371, 1465, 17372864, 2955, 3041.

Example 2-9

Preparation of ethyl (1-methyl-2-cyclopentenyl)acetate (2: R=Et; $X_1$, $X_3$, $X_4$, $X_5$, $X_6$, $X_7$=H; $X_2$=Me)

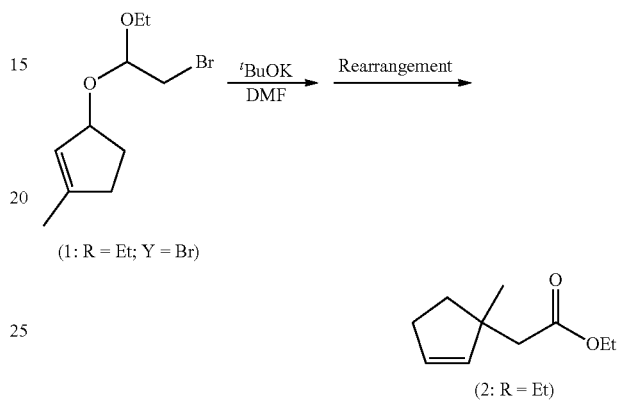

The procedures of Example 2-1 were repeated with the exception that bromoacetaldehyde ethyl 3-methyl-2-cyclopentenyl acetal (1: R=Et; $X_1$, $X_3$, $X_4$, $X_5$, $X_6$, $X_7$=H; $X_2$=Me; Y=Br) (24.92 g: 0.100 mol, purity 89.9%) obtained in Example 1-7 was used instead of bromoacetaldehyde ethyl 3,4,4-trimethyl-2-cyclopentenyl acetal (1: R=Et; $X_1$, $X_5$, $X_6$, $X_7$=H; $X_2$, $X_3$, $X_4$=Me; Y=Br) as a reaction substrate used in Example 2-1, and that the resulting crude product was purified by distillation at a reduced pressure instead of silica gel chromatography used in Example 2-1, so that obtained was ethyl (1-methyl-2-cyclopentenyl)acetate (2: R=Et; $X_1$, $X_3$, $X_4$, $X_5$, $X_6$, $X_7$=H; $X_2$=Me) (12.21 g: 0.073 mol, yield 72.6%, purity 97.6%).

The following are various spectrum data of ethyl (1-methyl-2-cyclopentenyl)acetate (2: R=Et; $X_1$, $X_3$, $X_4$, $X_5$, $X_6$, $X_7$=H; $X_2$=Me) thus prepared.

Nuclear magnetic resonance spectrum: $^1$H-NMR (600 MHz, CDCl$_3$): δ 1.14 (3H, s), 1.25 (3H, t, J=6.9 Hz), 1.67 (1H, dq, J=8.0, 6.0 Hz), 1.93 (1H, dq, J=8.4, 6.6 Hz), 2.32-2.37 (m, 4H), 4.11 (2H, q, J=5.4), 5.62-5.66 (2H, m) ppm. $^{13}$C-NMR (150 MHz, CDCl$_3$): δ 14.44, 26.45, 31.56, 37.15, 45.86, 47.51, 60.11, 129.47, 139.19, 172.38 ppm.

Mass spectrum EI (70 eV): m/z 168 (M$^+$), 139, 122, 107, 94, 81, 67, 53, 41, 39, 29.

Infrared absorption spectrum (D-ATR): ν (cm$^{-1}$) 739, 1035, 1120, 1290, 1317, 1340, 1367, 1454, 1733, 2852, 2868, 2957, 3051.

Example 3

The following Example 3-1 to Example 3-5 describe a process for preparing (2-cyclopentenyl)acetic acid compounds (3), as shown in the following reaction formula.

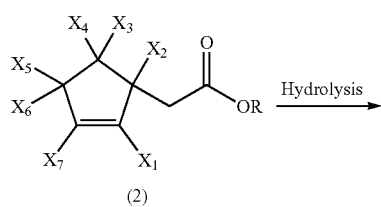

(2)

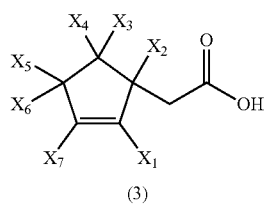

(3)

Example 3-1

Preparation of (1,5,5-trimethyl-2-cyclopentenyl)acetic acid (3: $X_1$, $X_5$, $X_6$, $X_7$=H; $X_2$, $X_3$, $X_4$=Me)

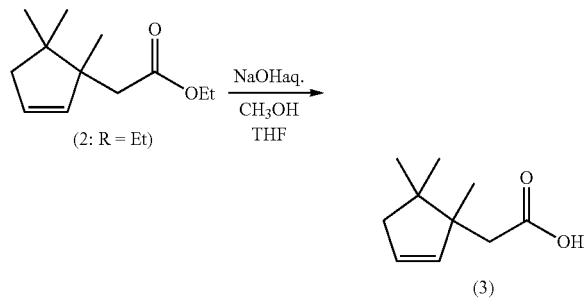

Air in a reactor equipped with a stirrer, a condenser, and a thermometer was purged with nitrogen. Then, to the reactor were added ethyl (1,5,5-trimethyl-2-cyclopentenyl)acetate (2: R=Et; $X_1$, $X_5$, $X_6$, $X_7$=H; $X_2$, $X_3$, $X_4$=Me) (19.63 g: 0.100 mol, purity 82.2%) obtained according to Example 2-1, methanol ($CH_3OH$) (70.0 g), and tetrahydrofuran (THF) (150.0 g), and then heated to a liquid temperature of 50° C. to 55° C. An aqueous 5 wt % sodium hydroxide solution (NaOH aq.) (380.0 g: 0.475 mol) was added to the mixture whose temperature was maintained at a liquid temperature of 50° C. to 55° C. over 2 hours. After the completion of the addition, the mixture was stirred at a liquid temperature of 55 to 60° C. for 10 hours.

After the completion of the stirring, the reaction mixture was cooled to a liquid temperature of 25° C. to 30° C., extracted with n-hexane (100.0 g), and layer-separated into an organic layer and an aqueous layer. To the aqueous layer was added dropwise 20 wt % hydrochloric acid (157.0 g) at a liquid temperature of 0° C. to 10° C. to make the mixture acidic. The mixture was then extracted with n-hexane (150.0 g) and layer-separated into an organic layer and an aqueous layer. The obtained organic layer was washed twice with an aqueous 15 wt % sodium chloride solution (500.0 g). The solvent was removed from the washed organic layer at a reduced pressure to obtain (1,5,5-trimethyl-2-cyclopentenyl)acetic acid (3: $X_1$, $X_5$, $X_6$, $X_7$=H; $X_2$, $X_3$, $X_4$=Me) (16.76 g: 0.099 mol, yield 99.6%, purity 93.2%).

(1,5,5-Trimethyl-2-cyclopentenyl)acetic acid (3: $X_1$, $X_5$, $X_6$, $X_7$=H; $X_2$, $X_3$, $X_4$=Me) thus prepared had a sufficient purity to be used without purification.

The following are various spectrum data of (1,5,5-trimethyl-2-cyclopentenyl)acetic acid (3: $X_1$, $X_5$, $X_6$, $X_7$=H; $X_2$, $X_3$, $X_4$=Me) thus prepared.

Nuclear magnetic resonance spectrum: $^1$H-NMR (500 MHz, $CDCl_3$): δ 0.94 (3H, s), 0.97 (3H, s), 1.02 (3H, s), 2.12 (1H, dt, J=16.1, 2.0 Hz), 2.18 (1H, dt, J=16.1, 2.3 Hz), 2.23 (1H, d, J=13.8 Hz), 2.36 (1H, d, J=13.8 Hz), 5.66 (1H, dt, J=6.1, 2.4 Hz), 5.80 (1H, dt, J=6.1, 1.9 Hz), 11.53 (1H, br) ppm. $^{13}$C-NMR (126 MHz, $CDCl_3$): δ 19.65, 24.02, 24.37, 40.37, 44.13, 46.58, 49.70, 128.14, 138.44, 179.96 ppm.

Mass spectrum EI (70 eV): m/z 168 ($M^+$), 153, 135, 109, 93, 91, 79, 67, 55, 41, 27.

Infrared absorption spectrum (D-ATR): ν ($cm^{-1}$) 661, 716, 741, 954, 1137, 1199, 1235, 1295, 1374, 1386, 1409, 1449, 1706, 2844, 2966, 3053.

Example 3-2

Preparation of (1,5,5-trimethyl-2-cyclopentenyl)acetic acid (3: $X_1$, $X_5$, $X_6$, $X_7$=H; $X_2$, $X_3$, $X_4$=Me)

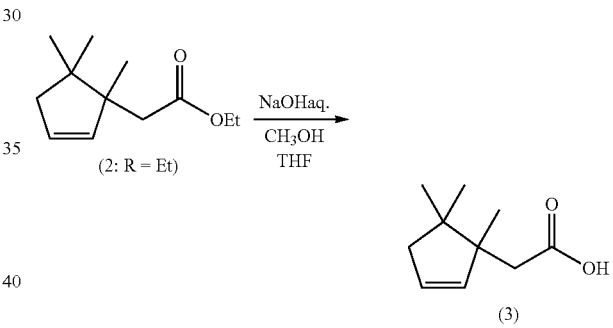

The procedures of Example 3-1 were repeated with the exception that crude ethyl (1,5,5-trimethyl-2-cyclopentenyl)acetate (2: R=Et; $X_1$, $X_5$, $X_6$, $X_7$=H; $X_2$, $X_3$, $X_4$=Me) (9.81 g: 0.050 mol, purity 41.8%) obtained according to Example 2-1 was used as a reaction substrate, so that obtained was (1,5,5-trimethyl-2-cyclopentenyl)acetic acid (3: $X_1$, $X_5$, $X_6$, $X_7$=H; $X_2$, $X_3$, $X_4$=Me) (8.09 g: 0.048 mol, yield 96.2%, purity 96.1%).

(1,5,5-Trimethyl-2-cyclopentenyl)acetic acid (3: $X_1$, $X_5$, $X_6$, $X_7$=H; $X_2$, $X_3$, $X_4$=Me) thus prepared had a sufficient purity to be used without purification.

The various spectrum data of (1,5,5-trimethyl-2-cyclopentenyl)acetic acid (3: $X_1$, $X_5$, $X_6$, $X_7$=H; $X_2$, $X_3$, $X_4$=Me) thus prepared were the same as those determined in Example 3-1.

The result of Example 3-2 shows that even if ethyl (1,5,5-trimethyl-2-cyclopentenyl)acetate (2: R=Et; $X_1$, $X_5$, $X_6$, $X_7$=H; $X_2$, $X_3$, $X_4$=Me) has a low purity, the purity of (1,5,5-trimethyl-2-cyclopentenyl)acetic acid (3: $X_1$, $X_5$, $X_6$, $X_7$=H; $X_2$, $X_3$, $X_4$=Me) thus prepared can be increased by alkali-extraction with an aqueous sodium hydroxide solution used in the hydrolysis to transfer impurities into an aqueous layer.

Example 3-3

Preparation of (1,2-dimethyl-2-cyclopentenyl)acetic acid (3: $X_3$, $X_4$, $X_5$, $X_6$, $X_7$=H; $X_1$, $X_2$=Me)

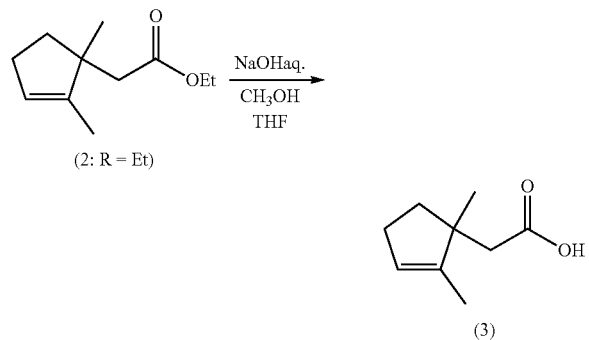

The procedures of Example 3-1 were repeated with the exception that ethyl (1,2-dimethyl-2-cyclopentenyl)acetate (2: R=Et; $X_3$, $X_4$, $X_5$, $X_6$, $X_7$=H; $X_1$, $X_2$=Me) (18.23 g: 0.100 mol, purity 89.6%) obtained according to Example 2-7 was used instead of ethyl (1,5,5-trimethyl-2-cyclopentenyl)acetate (2: R=Et; $X_1$, $X_5$, $X_6$, $X_7$=H; $X_2$, $X_3$, $X_4$=Me) as a reaction substrate used in Example 3-1, so that obtained was (1,2-dimethyl-2-cyclopentenyl)acetic acid (3: $X_3$, $X_4$, $X_5$, $X_6$, $X_7$=H; $X_1$, $X_2$=Me) (15.34 g: 0.099 mol, yield 99.5%, purity 98.6%).

(1,2-Dimethyl-2-cyclopentenyl)acetic acid (3: $X_3$, $X_4$, $X_5$, $X_6$, $X_7$=H; $X_1$, $X_2$=Me) thus prepared had a sufficient purity to be used without purification.

The following are various spectrum data of (1,2-dimethyl-2-cyclopentenyl)acetic acid (3: $X_3$, $X_4$, $X_5$, $X_6$, $X_7$=H; $X_1$, $X_2$=Me) thus prepared.

Nuclear magnetic resonance spectrum: $^1$H-NMR (600 MHz, CDCl$_3$): δ 1.13 (3H, s), 1.63 (3H, q, J=1.8 Hz), 1.71-1.75 (1H, m), 2.11-2.16 (1H, m), 2.20-2.23 (2H, m), 2.30 (1H, d, J=13.2 Hz), 2.39 (1H, d, J=13.8 Hz), 5.32 (1H, br d, J=1.2 Hz), 10.01 (1H, br s) ppm. $^{13}$C-NMR (150 MHz, CDCl$_3$): δ 12.46, 24.87, 29.32, 37.11, 43.32, 48.46, 124.99, 145.34, 178.88 ppm.

Mass spectrum EI (70 eV): m/z 154 (M$^+$), 139, 121, 94, 92, 79, 67, 55, 41, 39, 27.

Infrared absorption spectrum (ATR): ν(cm$^{-1}$) 475, 664, 823, 938, 1021, 1098, 1130, 1190, 1236, 1288, 1312, 1379, 1408, 1442, 1705, 2854, 2934, 2961, 3039.

Example 3-4

Preparation of (4,4-dimethyl-2-cyclopentenyl)acetic acid (3: $X_1$, $X_2$, $X_3$, $X_4$, $X_7$=H; $X_5$, $X_6$=Me)

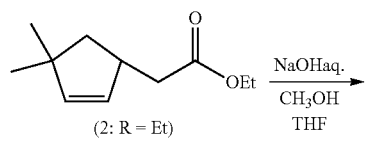

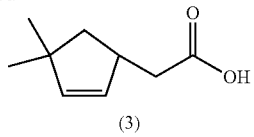

The procedures of Example 3-1 were repeated with the exception that ethyl (4,4-dimethyl-2-cyclopentenyl)acetate (2: R=Et; $X_1$, $X_2$, $X_3$, $X_4$, $X_7$=H; $X_5$, $X_6$=Me) (18.23 g: 0.100 mol, purity 82.1%) obtained according to Example 2-8 was used instead of ethyl (1,5,5-trimethyl-2-cyclopentenyl)acetate (2: R=Et; $X_1$, $X_5$, $X_6$, $X_7$=H; $X_2$, $X_3$, $X_4$=Me) as a reaction substrate used in Example 3-1, so that obtained was (4,4-dimethyl-2-cyclopentenyl)acetic acid (3: R=Et; $X_1$, $X_2$, $X_3$, $X_4$, $X_7$=H; $X_5$, $X_6$=Me) (15.05 g: 0.098 mol, yield 97.6%, purity 94.5%).

(4,4-Dimethyl-2-cyclopentenyl)acetic acid (3: R=Et; $X_1$, $X_2$, $X_3$, $X_4$, $X_7$=H; $X_5$, $X_6$=Me) thus prepared had a sufficient purity to be used without purification.

The following are various spectrum data of (4,4-dimethyl-2-cyclopentenyl)acetic acid (3: R=Et; $X_1$, $X_2$, $X_3$, $X_4$, $X_7$=H; $X_5$, $X_6$=Me) thus prepared.

Nuclear magnetic resonance spectrum: $^1$H-NMR (600 MHz, CDCl$_3$): δ 1.04 (3H, s), 1.10 (3H, s), 1.30 (1H, dd, J=12.6, 7.2 Hz), 2.03 (1H, dd, J=12.6, 7.8 Hz), 2.35 (1H, dd, J=15.3, 8.1 Hz), 2.47 (1H, dd, J=15.6, 7.2 Hz), 3.17 (1H, quin, J=7.4 Hz), 5.50 (1H, dd, J=6.0, 1.8 Hz), 5.57 (1H, dd, J=5.7, 2.1 Hz), 9.40 (1H, brs) ppm. $^{13}$C-NMR (126 MHz, CDCl$_3$): δ 28.46, 29.95, 40.87, 41.52, 45.42, 45.77, 130.49, 142.77, 179.20 ppm.

Mass spectrum EI (70 eV): m/z 154 (M$^+$), 139, 121, 95, 94, 79, 77, 67, 55, 41, 39, 27.

Infrared absorption spectrum (ATR): ν (cm$^{-1}$) 675, 756, 936, 1044, 1212, 1281, 1361, 1409, 1709, 2865, 2954, 3041.

Example 3-5

Preparation of (1-methyl-2-cyclopentenyl)acetic acid (3: $X_1$, $X_3$, $X_4$, $X_5$, $X_6$, $X_7$=H; $X_2$=Me)

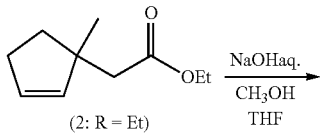

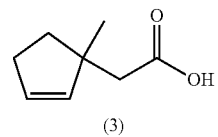

The procedures of Example 3-1 were repeated with the exception that ethyl (1-methyl-2-cyclopentenyl)acetate (2: R=Et; $X_1$, $X_3$, $X_4$, $X_5$, $X_6$, $X_7$=H; $X_2$=Me) (16.82 g: 0.100 mol, purity 86.9%) obtained according to Example 2-9 was used instead of ethyl (1,5,5-trimethyl-2-cyclopentenyl)acetate (2: R=Et; $X_1$, $X_5$, $X_6$, $X_7$=H; $X_2$, $X_3$, $X_4$=Me) as a reaction substrate used in Example 3-1, so that obtained was (1-methyl-2-cyclopentenyl)acetic acid (3: $X_1$, $X_3$, $X_4$, $X_5$, $X_6$, $X_7$=H; $X_2$=Me) (13.30 g: 0.095 mol, yield 94.9%, purity 98.0%).

(1-Methyl-2-cyclopentenyl)acetic acid (3: $X_1$, $X_3$, $X_4$, $X_5$, $X_6$, $X_7$=H; $X_2$=Me) thus prepared had a sufficient purity to be used without purification.

The following are various spectrum data of (1-methyl-2-cyclopentenyl)acetic acid (3: $X_1$, $X_3$, $X_4$, $X_5$, $X_6$, $X_7$=H; $X_2$=Me) thus prepared.

Nuclear magnetic resonance spectrum: $^1$H-NMR (500 MHz, CDCl$_3$): δ 1.17 (3H, s), 1.67-1.73 (1H, m), 1.91-1.96 (1H, m), 2.34-2.43 (4H, m), 5.64-5.68 (2H, m), 11.56 (1H, brs) ppm. $^{13}$C-NMR (126 MHz, CDCl$_3$): δ 26.12, 31.37, 37.10, 45.48, 47.17, 129.64, 138.74, 178.94 ppm.

Mass spectrum EI (70 eV): m/z 140 (M$^+$), 122, 107, 81, 80, 79, 53, 41, 39.

Infrared absorption spectrum (ATR): ν (cm$^{-1}$) 692, 737, 924, 1100, 1127, 1246, 1289, 1315, 1353, 1375, 1409, 1706, 2868, 2957, 3051.

COMPARATIVE EXAMPLES

The following Comparative Examples 1 and 2 describe a process, described in Non-Patent Literature 6, for preparing ethyl (1,5,5-trimethyl-2-cyclopentenyl)acetate (2: R=Et; $X_1$, $X_5$, $X_6$, $X_7$=H; $X_2$, $X_3$, $X_4$=Me) from 3,4,4-trimethyl-2-cyclopenten-1-ol (5: $X_1$, $X_5$, $X_6$, $X_7$=H; $X_2$, $X_3$, $X_4$=Me) using a Johnson-Claisen rearrangement reaction and a process, described in Non-Patent Literature 6, for preparing ethyl (1,2-dimethyl-2-cyclopentenyl)acetate (2: R=Et; $X_3$, $X_4$, $X_5$, $X_6$, $X_7$=H; $X_1$, $X_2$=Me) from 2,3-dimethyl-2-cyclopenten-1-ol (5: $X_3$, $X_4$, $X_5$, $X_6$, $X_7$=H; $X_1$, $X_2$=Me) using a Johnson-Claisen rearrangement reaction described in Non-Patent Literature 6.

Comparative Example 1

Preparation of ethyl (1,5,5-trimethyl-2-cyclopentenyl)acetate (2: R=Et; $X_1$, $X_5$, $X_6$, $X_7$=H; $X_2$, $X_3$, $X_4$=Me)

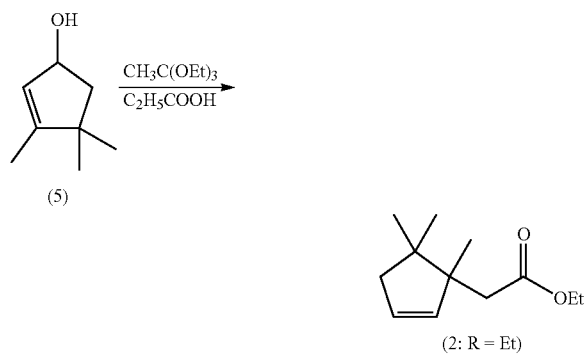

Air in a reactor equipped with a stirrer, a condenser, a distillation tower, and a thermometer was purged with nitrogen. Then, to the reactor were added 3,4,4-trimethyl-2-cyclopenten-1-ol (5: $X_1$, $X_5$, $X_6$, $X_7$=H; $X_2$, $X_3$, $X_4$=Me) (12.62 g: 0.100 mol, purity 94.9%), triethyl orthoacetate (CH$_3$C(OEt)$_3$) (81.12 g: 0.500 mol), and propionic acid (C$_2$H$_5$COOH) (0.74 g: 0.010 mol), and the mixture was then stirred at a liquid temperature of 140° C. to 145° C. for 38 hours while distilling the refluxing ethanol off from a head of a fractional distillation tower. After the completion of the stirring, the reaction mixture was cooled to a liquid temperature of 20° C. to 25° C. The excess triethyl orthoacetate was removed from the reaction mixture at a reduced pressure, and the crude product was then purified by silica gel column chromatography to obtain ethyl (1,5,5-trimethyl-2-cyclopentenyl)acetate (2: R=Et; $X_1$, $X_5$, $X_6$, $X_7$=H; $X_2$, $X_3$, $X_4$=Me) (5.95 g: 0.030 mol, yield 30.3%).

The $^1$H-NMR (nuclear magnetic resonance spectrum) and mass spectrum data of ethyl (1,5,5-trimethyl-2-cyclopentenyl)acetate (2: R=Et; $X_1$, $X_5$, $X_6$, $X_7$=H; $X_2$, $X_3$, $X_4$=Me) thus prepared were the same as those determined in Example 2-1.

The yield of ethyl (1,5,5-trimethyl-2-cyclopentenyl)acetate (2: R=Et; $X_1$, $X_5$, $X_6$, $X_7$=H; $X_2$, $X_3$, $X_4$=Me) obtained in Comparative Example 1 was 30.3% which was lower than the yield of in Example 2-1 (49.7%), the yield of 47.8% in Example 2-2, the yield of 43.9% in Example 2-3, and the yield of 48.4% in Example 2-4.

Comparative Example 2

Preparation of ethyl (1,2-dimethyl-2-cyclopentenyl)acetate (2: R=Et; $X_3$, $X_4$, $X_5$, $X_6$, $X_7$=H; $X_1$, $X_2$=Me)

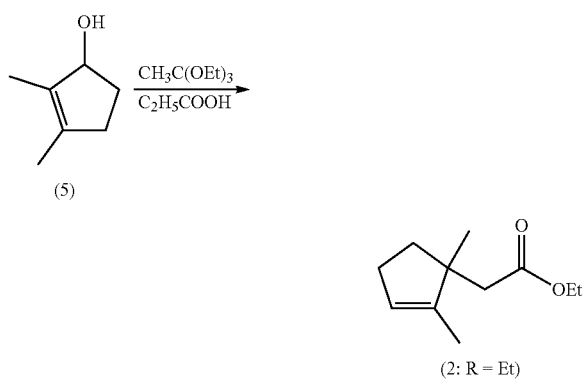

The procedures of Comparative Example 1 were repeated with the exception that 2,3-dimethyl-2-cyclopenten-1-ol (5: $X_3$, $X_4$, $X_5$, $X_6$, $X_7$=H; $X_1$, $X_2$=Me) (11.22 g: 0.100 mol, purity 93.6%) was used instead of 3,4,4-trimethyl-2-cyclopenten-1-ol (5: $X_1$, $X_5$, $X_6$, $X_7$=H; $X_2$, $X_3$, $X_4$=Me) as a reaction substrate used in Comparative Example 1, so that obtained was ethyl (1,2-dimethyl-2-cyclopentenyl)acetate (2: R=Et; $X_3$, $X_4$, $X_5$, $X_6$, $X_7$=H; $X_1$, $X_2$=Me) (7.49 g: 0.041 mol, yield 41.1%).

The $^1$H-NMR (nuclear magnetic resonance spectrum) and mass spectrum data of ethyl (1,2-dimethyl-2-cyclopentenyl)acetate (2: R=Et; $X_3$, $X_4$, $X_5$, $X_6$, $X_7$=H; $X_1$, $X_2$=Me) thus prepared were the same as those determined in Example 2-7.

The yield of ethyl (1,2-dimethyl-2-cyclopentenyl)acetate (2: R=Et; $X_3$, $X_4$, $X_5$, $X_6$, $X_7$=H; $X_1$, $X_2$=Me) obtained in Comparative Example 2 was 41.1% which was lower than the yield of 83.0% in Example 2-7.

The invention claimed is:

1. A process for preparing a (2-cyclopentenyl)acetate ester compound of the following general formula (2):

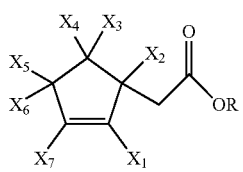

(2)

wherein R represents a linear or branched alkyl group having 1 to 4 carbon atoms, and $X_1$ to $X_7$ represent, independently of each other, a hydrogen atom or a methyl group, with the proviso that one to three among $X_1$ to $X_7$ represent a methyl group and the remaining represent a hydrogen atom, the process comprising:

subjecting a haloacetaldehyde alkyl 2-cyclopentenyl acetal compound of the following general formula (1):

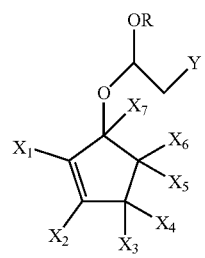

(1)

wherein R is as defined above, $X_1$ to $X_7$ are as selected in the general formula (2), respectively, and Y represents a halogen atom, to a dehydrohalogenation reaction in the presence of a base, followed by a rearrangement reaction to form the (2-cyclopentenyl)acetate ester compound (2).

2. A process for preparing a (2-cyclopentenyl)acetic acid compound of the following general formula (3):

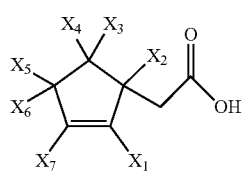

(3)

wherein $X_1$ to $X_7$ are as selected in the general formula (1), respectively, the process comprising:

the process according to claim 1 for preparing the (2-cyclopentenyl)acetate ester compound (2); and hydrolyzing the (2-cyclopentenyl)acetate ester compound (2) to form the (2-cyclopentenyl)acetic acid compound (3).

3. A process for preparing a (2-cyclopentenyl)acetate ester compound of the following general formula (2):

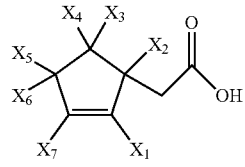

(3)

wherein R represents a linear or branched alkyl group having 1 to 4 carbon atoms, $X_1$ to $X_7$ are as selected in the general formula (1), respectively, the process comprising:

halogenating an alkyl vinyl ether compound of the following general formula (4):

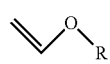

(4)

wherein R represents a linear or branched alkyl group having 1 to 4 carbon atoms, with a halogenating agent to form a halide; and subjecting the halide to a substitution reaction with a 2-cyclopenten-1-ol compound of the following general formula (5):

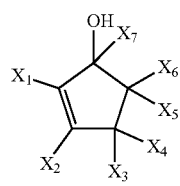

(5)

wherein $X_1$ to $X_7$ represent, independently of each other, a hydrogen atom or a methyl group, with the proviso that one to three among $X_1$ to $X_7$ represent a methyl group and the remaining represent a hydrogen atom, to form a haloacetaldehyde alkyl 2-cyclopentenyl acetal compound of the following general formula (1):

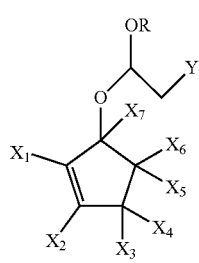

(1)

wherein R represents a linear or branched alkyl group having 1 to 4 carbon atoms, $X_1$ to $X_7$ are as selected in the general formula (5), respectively, and Y represents a halogen atom; and subjecting the haloacetaldehyde alkyl 2-cyclopentenyl acetal compound (1) to a dehydrohalogenation reaction in the presence of a base, followed by a rearrangement reaction to form the (2-cyclopentenyl) acetate ester compound (2).

4. A process for preparing a (2-cyclopentenyl)acetic acid compound of the following general formula (3):

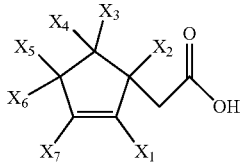
(3)

wherein $X_1$ to $X_7$ are as selected in the general formula (1), respectively, the process comprising:
the process according to claim 3 for preparing the (2-cyclopentenyl)acetate ester compound (2); and
hydrolyzing the (2-cyclopentenyl)acetate ester compound (2) to form the (2-cyclopentenyl)acetic acid compound (3).

5. A haloacetaldehyde alkyl 2-cyclopentenyl acetal compound of the following general formula (1):

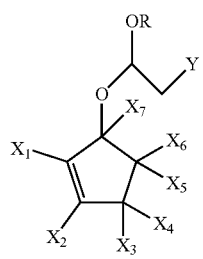
(1)

wherein:
R represents a linear or branched alkyl group having 1 to 4 carbon atoms;
$X_1$ to $X_7$ represent, independently of each other, a hydrogen atom or a methyl group, with the proviso that one to three among $X_1$ to $X_7$ represent a methyl group and the remaining represent a hydrogen atom, with the proviso that when $X_1$ represents a methyl group, one or two of $X_2$ to $X_7$ represent a methyl group, and with the proviso that when $X_1$ and $X_2$ are methyl and $X_3$ to $X_7$ are hydrogen, R is not ethyl; and
Y represents a halogen atom.

6. The haloacetaldehyde alkyl 2-cyclopentenyl acetal compound according to claim 5, wherein $X_1$ represents a hydrogen atom and one to three of $X_2$ to $X_7$ represents a methyl group.

7. The haloacetaldehyde alkyl 2-cyclopentenyl acetal compound according to claim 5, wherein two or three of $X_1$ to $X_7$ represent a methyl group.

8. The haloacetaldehyde alkyl 2-cyclopentenyl acetal compound according to claim 5, wherein $X_1$, $X_5$, $X_6$, and $X_7$ represent a hydrogen atom; and $X_2$, $X_3$, and $X_4$ represent a methyl group.

9. The haloacetaldehyde alkyl 2-cyclopentenyl acetal compound according to claim 5, wherein $X_3$, $X_4$, $X_5$, $X_6$, and $X_7$ represent a hydrogen atom; and $X_1$ and $X_2$ represent a methyl group.

10. The haloacetaldehyde alkyl 2-cyclopentenyl acetal compound according to claim 5, wherein $X_1$, $X_2$, $X_3$, $X_4$, and $X_7$ represent a hydrogen atom; and $X_5$ and $X_6$ represent a methyl group.

11. The haloacetaldehyde alkyl 2-cyclopentenyl acetal compound according to claim 5, wherein $X_1$, $X_3$, $X_4$, $X_5$, $X_6$, and $X_7$ represent a hydrogen atom; and $X_2$ represents a methyl group.

12. The haloacetaldehyde alkyl 2-cyclopentenyl acetal compound according to claim 5, wherein Y represents a bromine atom.

13. The haloacetaldehyde alkyl 2-cyclopentenyl acetal compound according to claim 8, wherein Y represents a bromine atom.

14. The haloacetaldehyde alkyl 2-cyclopentenyl acetal compound according to claim 9, wherein Y represents a bromine atom.

15. The haloacetaldehyde alkyl 2-cyclopentenyl acetal compound according to claim 10, wherein Y represents a bromine atom.

16. The haloacetaldehyde alkyl 2-cyclopentenyl acetal compound according to claim 11, wherein Y represents a bromine atom.

* * * * *

UNITED STATES PATENT AND TRADEMARK OFFICE
CERTIFICATE OF CORRECTION

PATENT NO. : 11,840,511 B2
APPLICATION NO. : 17/805513
DATED : December 12, 2023
INVENTOR(S) : Yamashita et al.

It is certified that error appears in the above-identified patent and that said Letters Patent is hereby corrected as shown below:

In the Specification

Column 3, Lines 16-17: Please remove the paragraph break between "specification)." and "Thus,"

Column 9, Line 57: Please insert a paragraph break between "acetal;" and "chloroacetaldehyde"

Column 22, Line 43: Please correct "product]+" to read --product]÷--

Column 22, Lines 50-51: Please correct "0.25 μmx0.25 mm>x30 m" to read --0.25 μm x 0.25 mmφ x 30 m--

In the Claims

Column 44, Lines 1-8, Claim 3: Please delete structure and replace with the following:

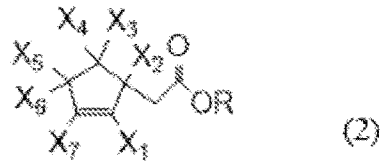

Signed and Sealed this
Twenty-sixth Day of March, 2024

Katherine Kelly Vidal
*Director of the United States Patent and Trademark Office*